United States Patent
Schulman et al.

(10) Patent No.: US 6,829,508 B2
(45) Date of Patent: Dec. 7, 2004

(54) ELECTRICALLY SENSING AND STIMULATING SYSTEM FOR PLACEMENT OF A NERVE STIMULATOR OR SENSOR

(75) Inventors: Joseph H. Schulman, Santa Clarita, CA (US); Ralph M. Weisner, Woodland Hills, CA (US); David L. Canfield, Lake Hughes, CA (US); Kate E. Fey, Santa Clarita, CA (US); Charles L. Byers, Canyon Country, CA (US)

(73) Assignee: Alfred E. Mann Foundation for Scientific Research, Valencia, CA (US)

( * ) Notice: Subject to any disclaimer, the term of this patent is extended or adjusted under 35 U.S.C. 154(b) by 371 days.

(21) Appl. No.: 10/116,619

(22) Filed: Apr. 4, 2002

(65) Prior Publication Data

US 2003/0078643 A1 Apr. 24, 2003

Related U.S. Application Data

(60) Provisional application No. 60/330,165, filed on Oct. 19, 2001.

(51) Int. Cl.[7] .............................. A61N 1/05; A61N 1/36
(52) U.S. Cl. ..................................................... 607/116
(58) Field of Search .......................... 607/48, 115–116, 607/118, 150; 600/585, 546–548

(56) References Cited

U.S. PATENT DOCUMENTS

| 5,193,539 | A |  | 3/1993 | Schulman et al. ............ 607/61 |
|---|---|---|---|---|
| 5,193,540 | A |  | 3/1993 | Schulman et al. ............ 607/61 |
| 5,324,316 | A |  | 6/1994 | Schulman et al. ............ 607/61 |
| 5,405,367 | A |  | 4/1995 | Schulman et al. ............ 607/61 |
| 5,775,331 | A |  | 7/1998 | Raymond et al. ........... 600/554 |
| 5,779,642 | A |  | 7/1998 | Nightengale ................ 600/461 |
| 5,853,373 | A | * | 12/1998 | Griffith et al. .............. 600/554 |
| 6,051,017 | A | * | 4/2000 | Loeb et al. ..................... 607/1 |
| 6,061,596 | A |  | 5/2000 | Richmond et al. ............ 607/41 |
| 6,175,764 | B1 |  | 1/2001 | Loeb et al. ..................... 607/3 |
| 6,181,965 | B1 |  | 1/2001 | Loeb et al. ..................... 607/3 |
| 6,185,452 | B1 |  | 2/2001 | Schulman et al. ............ 604/20 |
| 6,185,455 | B1 |  | 2/2001 | Loeb et al. ..................... 607/3 |
| 6,208,894 | B1 |  | 3/2001 | Schulman et al. ............. 607/2 |
| 6,214,032 | B1 |  | 4/2001 | Loeb et al. ..................... 607/1 |
| 6,315,721 | B2 |  | 11/2001 | Schulman et al. .......... 600/301 |
| 6,345,202 | B2 |  | 2/2002 | Richmond et al. ............ 607/42 |
| 6,512,958 | B1 | * | 1/2003 | Swoyer et al. .............. 607/117 |

* cited by examiner

*Primary Examiner*—Carl Layno
(74) *Attorney, Agent, or Firm*—Gary D. Schnittgrund

(57) ABSTRACT

An electrically sensing and stimulating outer sheath for ensuring accurate surgical placement of a microsensor or a microstimulator near a nerve in living tissue is disclosed. The electrically sensing outer sheath may also be used to verify the function of the microstimulator or microsensor during surgical placement but before the outer sheath is removed. In the event that the microstimulator is not optimally placed near the nerve, or if the microstimulator is malfunctioning, this can be determined prior to removal of the outer sheath, thus reducing the possibility of nerve or tissue damage that might be incurred during a separate operation to remove the microstimulator.

41 Claims, 22 Drawing Sheets

ELECTRICALLY SENSING AND STIMULATING SYSTEM FOR PLACEMENT OF A NERVE STIMULATOR OR SENSOR

CROSS REFERENCE TO RELATED APPLICATION

This application claims the benefit of commonly assigned U.S. Provisional application No. 60/330,165, filed Oct. 19, 2001. This application is related to but in no way dependent on commonly assigned U.S. Patent application, System and Method for Removing Implanted Devices, filed on even date herewith and incorporated herein by reference.

FIELD OF THE INVENTION

This invention relates to placement of a nerve stimulator or sensor in living tissue.

BACKGROUND OF THE INVENTION

Microstimulators are small, implantable electrical devices that pass a small signal to living tissue in order to elicit a response from a nerve or muscle. Microsensors are similar electrical devices except that they detect electrical and other signals that are generated by living tissue. The term microstimulator is intended to apply equally to both microstimulators and microsensors. The use of microstimulators or microsensors which are implanted in living tissue to stimulate a muscle function by either stimulating a nerve or the muscle itself are well known. The microstimulators receive power and control signals by inductive coupling of magnetic fields generated by an extracorporeal antenna rather than requiring any electrical leads. See for example, U.S. Pat. Nos. 5,193,539; 5,193,540; 5,324,316; 5,405,367; 6,175,764; 6,181,965; 6,185,452; 6,185,455; 6,208,894; 6,214,032; and 6,315,721, each of which is incorporated in its entirety by reference herein. These microstimulators are particularly advantageous because they can be manufactured inexpensively and can be implanted non-surgically by injection. Additionally, each implanted microstimulator can be commanded, at will, to produce a well-localized electrical current pulse of a prescribed magnitude, duration and/or repetition rate sufficient to cause a smoothly graded contraction of the muscle in which the microstimulator is implanted.

While primarily designed to reanimate muscles so that they can carry out purposeful movements such as locomotion, the low cost, simplicity, safety and ease of implantation of these microstimulators suggests that they may additionally be used to conduct a broader range of therapies in which increased muscle strength, increased muscle fatigue resistance and/or increased muscle physical bulk are desirable; such as therapies directed to muscle disorders. For example, electrical stimulation of an immobilized muscle in a casted limb may be used to elicit isometric muscle contractions that prevent atrophy of the muscle for the duration of the casting period and facilitate rehabilitation after the cast is removed. Similarly, repeated activation of microstimulators injected into the shoulder muscles of patients suffering from stroke enable the paretic muscles to retain or develop bulk and tone, thus helping to offset the tendency for such patients to develop subluxation at the shoulder joint. Use of microstimulators to condition perineal muscles increases the bulk and strength of the musculature in order to maximize its ability to prevent urinary or fecal incontinence. See for example, U.S. Pat. No. 6,061,596, which is incorporated in its entirety by reference herein.

Microstimulators, as exemplified by the BION® of Advanced Bionics Corporation, are typically elongated devices with metallic electrodes at each end that deliver electrical current to the immediately surrounding living tissues. The microelectronic circuitry and inductive coils that control the electrical current applied to the electrodes are protected from the body fluids by a hermetically sealed capsule. This capsule is typically made of a rigid dielectric material, such as glass or ceramic, that transmits magnetic fields but is impermeable to water.

Often, while placing the miniature microstimulator in living tissue, the orientation of the microstimulator changes slightly such that the microstimulator is not in fact in electrical contact with the nerve, requiring reorientation of the microstimulator. The microstimulator may move at any point in the surgical implantation procedure. If the microstimulator has moved, it may be at a significant distance from the nerve that is to be stimulated. Consequently, more energy is needed from the microstimulator to stimulate the nerve, unless the microstimulator is repositioned closer to the nerve. While such microstimulators may be injected, the actual placement requires first locating the desired end point near the nerve or muscle. The known method of placement involves locating the nerve with an electric probe, placing a hollow implantation tool over the electric probe and removing the electric probe to allow the miniature microstimulator to be passed down the length of the hollow implantation tool. The implantation tool is then removed, leaving the microstimulator implanted at or near the desired location. If there is a problem with the function or location of the microstimulator, then additional surgery must be performed to remove or relocate the microstimulator, imposing risk, discomfort and potential tissue damage to the patient.

Using a known implantation tool, as disclosed in U.S. Pat. No. 6,214,032, to implant a microstimulator, may lead to the device being located remotely from the desired nerve. In this approach, an electrically stimulating trocar is first used to locate the desired nerve. The trocar is removed, after a cannula is slid along the trocar to be next to the nerve. Then the microstimulator is placed next to the nerve by inserting the microstimulator into the cannula and pushing the microstimulator to the end of the cannula, where it is ejected and is left behind, after the cannula is removed. The problem is that once the electrically stimulating trocar is removed, there is no way to detect movement of the cannula. Thus, the microstimulator may be left some distance from desired location, as was located by the stimulating trocar. This displacement from the optimum stimulating site unacceptably increases the power requirements and diminishes the battery life of the microstimulator.

Therefore, it is desired to have a method of implantation that ensures that the microstimulator is functioning properly and is implanted in an optimum position prior to removing the implantation tools that are utilized during surgery to place the microstimulator.

OBJECTS OF THE INVENTION

It is an object of the invention to locate an outer sheath near a nerve by monitoring muscle response from an electrical sensing or stimulating outer sheath.

It is an object of the invention to enable placement of a microstimulator or microsensor near a nerve by using an electrical path through the outer sheath.

It is an object of the invention to reliably place a microstimulator or microsensor near a nerve during surgery.

It is an object of the invention to verify that a microstimulator or microsensor is properly functioning during surgical placement of the microstimulator or microsensor.

It is an object of the invention to provide a tool for insertion of a microstimulator in living tissue.

It is an object of the invention to facilitate placement of a microstimulator in living tissue.

Other objects, advantages and novel features of the present invention will become apparent from the following detailed description of the invention when considered in conjunction with the accompanying drawings.

DETAILED DESCRIPTION OF THE PREFERRED EMBODIMENT

A. Two Part System for Insertion of a Microstimulator

A solution to the problems that have been encountered in precisely placing a microdevice in living tissue is to monitor the position of the implant device continuously by observing the muscle response to electrical stimulation during implantation of the microdevice, between the time when the probe is removed and when the microdevice is released. Loeb, et al. describe an alternative approach to placing a microstimulator near a nerve. See U.S. Pat. No. 6,214,032, which is incorporated herein in its entirety by reference. See also U.S. Pat. No. 6,345,202, which is incorporated herein in its entirety by reference, which discusses verifying the location of the insertion needle by electrical stimulation of a removable trocar within the hollow sheath of the needle.

Figure 1:
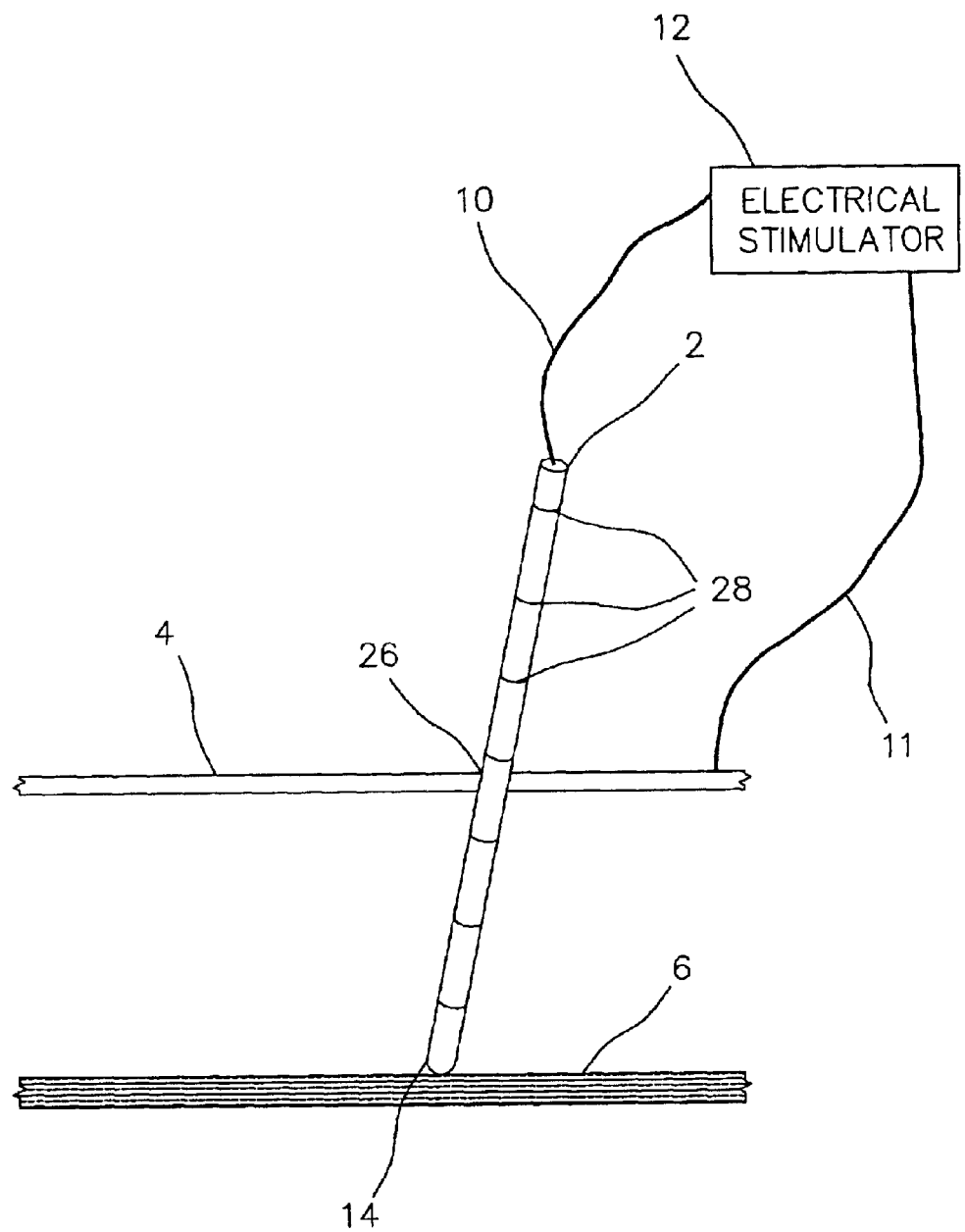
FIG. 1 illustrates a stimulating electrode near a nerve.

A preferred embodiment of the invention is illustrated in FIGS. 1–5, wherein FIG. 1 illustrates the electrode probe 2 locating the nerve 6 by electrically stimulating the nerve 6 and observing the muscle response. The electrical signal is generated by the electrical stimulator 12, e.g., a pulse generator. It is obvious that the electrode probe 2 could be a detector and electrical stimulator 12 could be a signal amplifier. The signal passes along electrode probe wire 10, along electrically insulated electrode probe 2 to conducting tip 14. Return electrode probe wire 11 preferably completes the electrical path by connecting between the skin 4 and electrical stimulator 12. Electrode probe 2 is electrically insulated along its entire length, except that the conducting tip 14 is not insulated, allowing the electrical signal to pass into the living tissue. Visual observation of the contracting muscle indicates when the conducting tip 14 is located next to nerve 6. Location marks 28, that circumscribes electrode probe 2, provides a visual indication of the precise location of the nerve.

Figure 2:
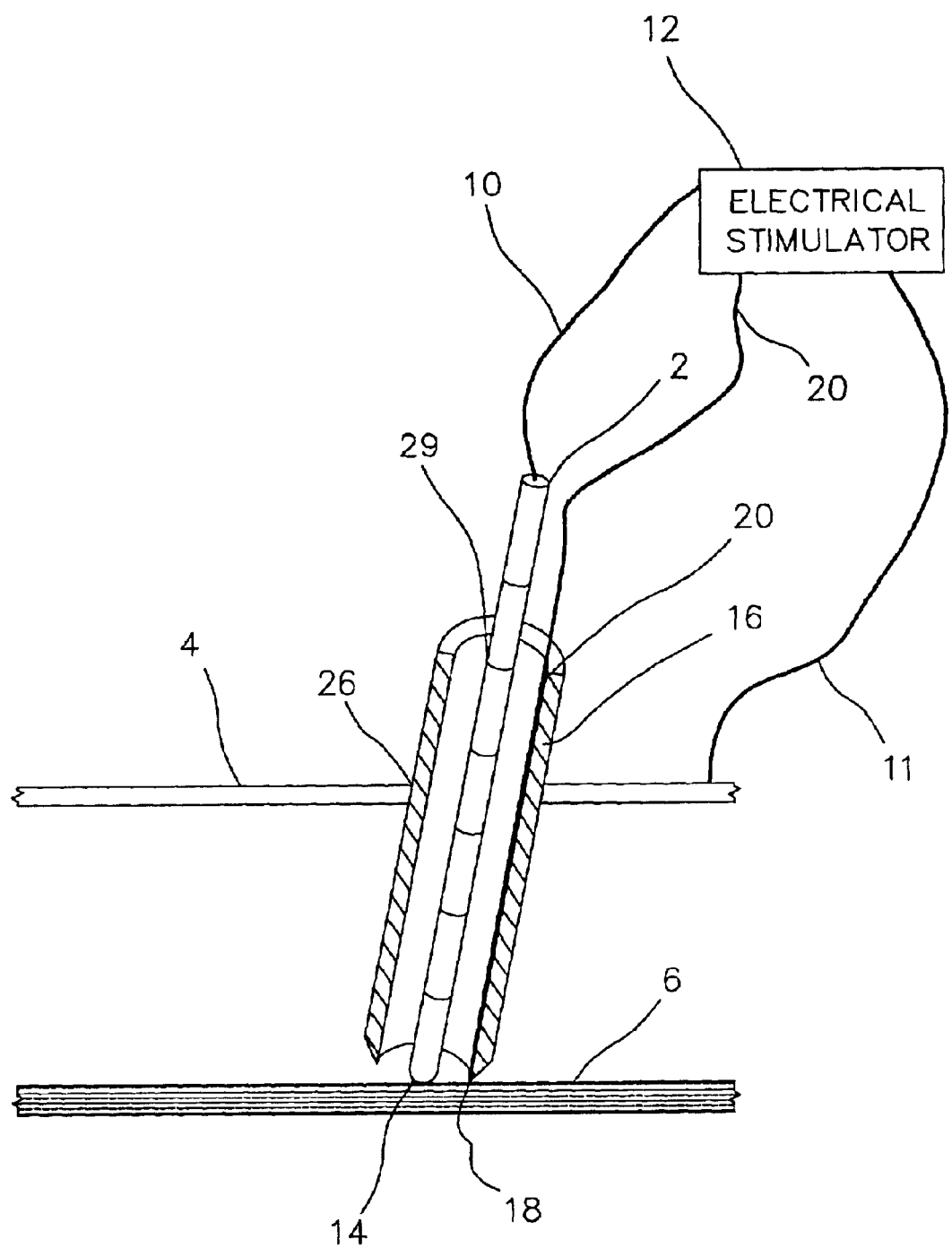
FIG. 2 illustrates an outer sheath with sheath electrode surrounding an electrode probe near a nerve.

After the nerve 6 is located, electrode probe wire 10 is detached from the electrode probe 2 and an outer sheath 16, as illustrated in FIG. 2, is slid over and along the electrode probe 2, to penetrate the living tissue. The outer sheath 16 is inserted until it aligns with depth indicator 29, a selected one of the location marks 28. The outer sheath 16 contains a sheath lead wire 20, which is electrically insulated along its length. The sheath lead wire 20 passes along the length of outer sheath 16, preferably on its inner diameter along the wall. The lead wire 20 terminates at the sheath electrode 18, which is preferably located on the end of the outer sheath 16 that contacts the nerve 6. The sheath electrode 18 preferably receives an electrical signal from the electrical stimulator 12 by a current that passes along sheath lead wire 20 to the sheath electrode 18. A return electrode is preferably attached to the skin 4 and the electrical circuit is completed by return electrode probe wire 11.

The outer sheath 16 is inserted to align with an electrode location mark 28 such that the sheath electrode 18 is located near the nerve 6. The position of the sheath 16 is optimized by electrically pulsing the nerve 6 and observing the response of the associated muscle. When electrode probe 2 is removed, the position of the outer sheath 16 is confirmed by electrically pulsing the nerve 6, as previously discussed.

Figure 3:
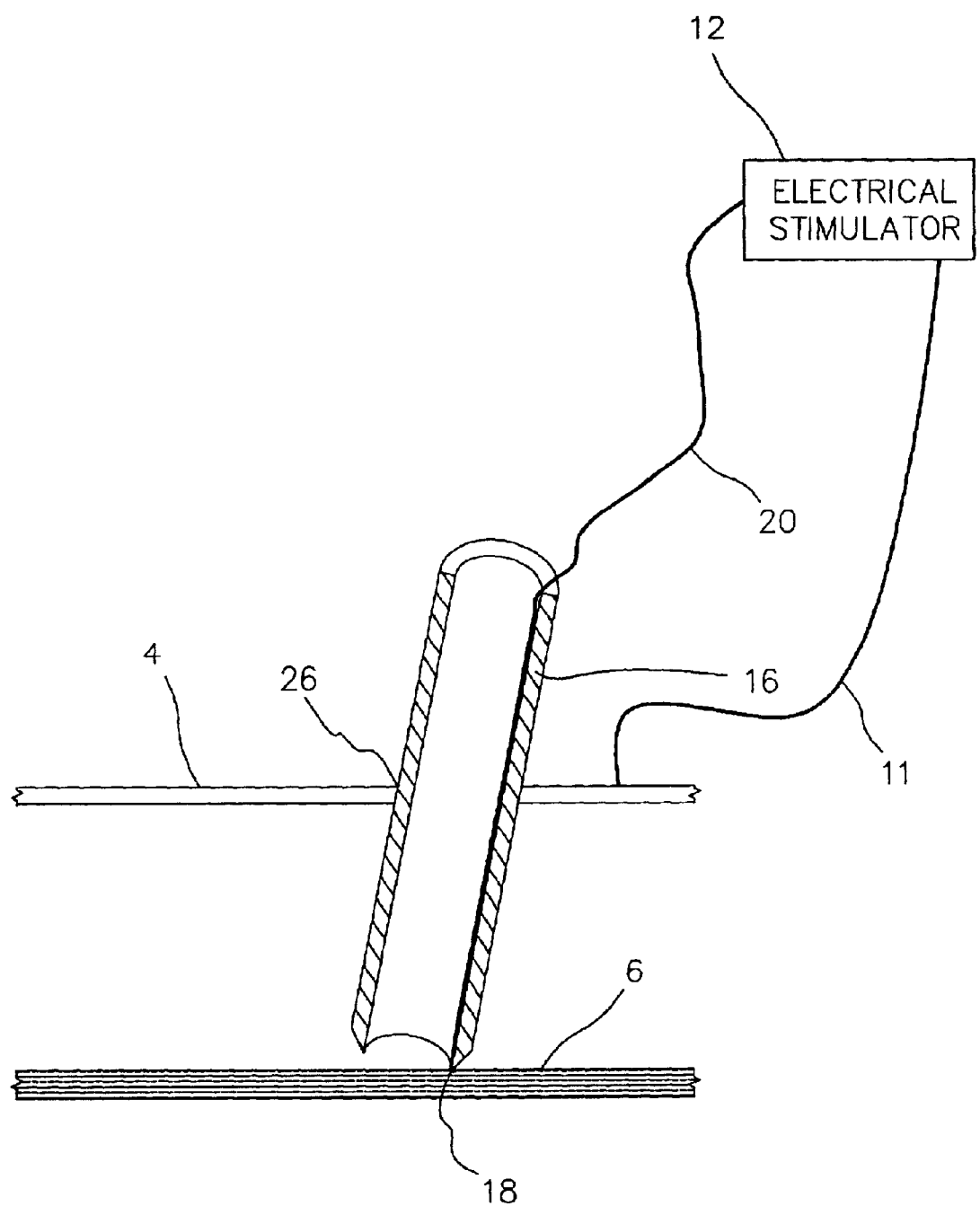
FIG. 3 illustrates an outer sheath with sheath electrode near a nerve.
Figure 4:
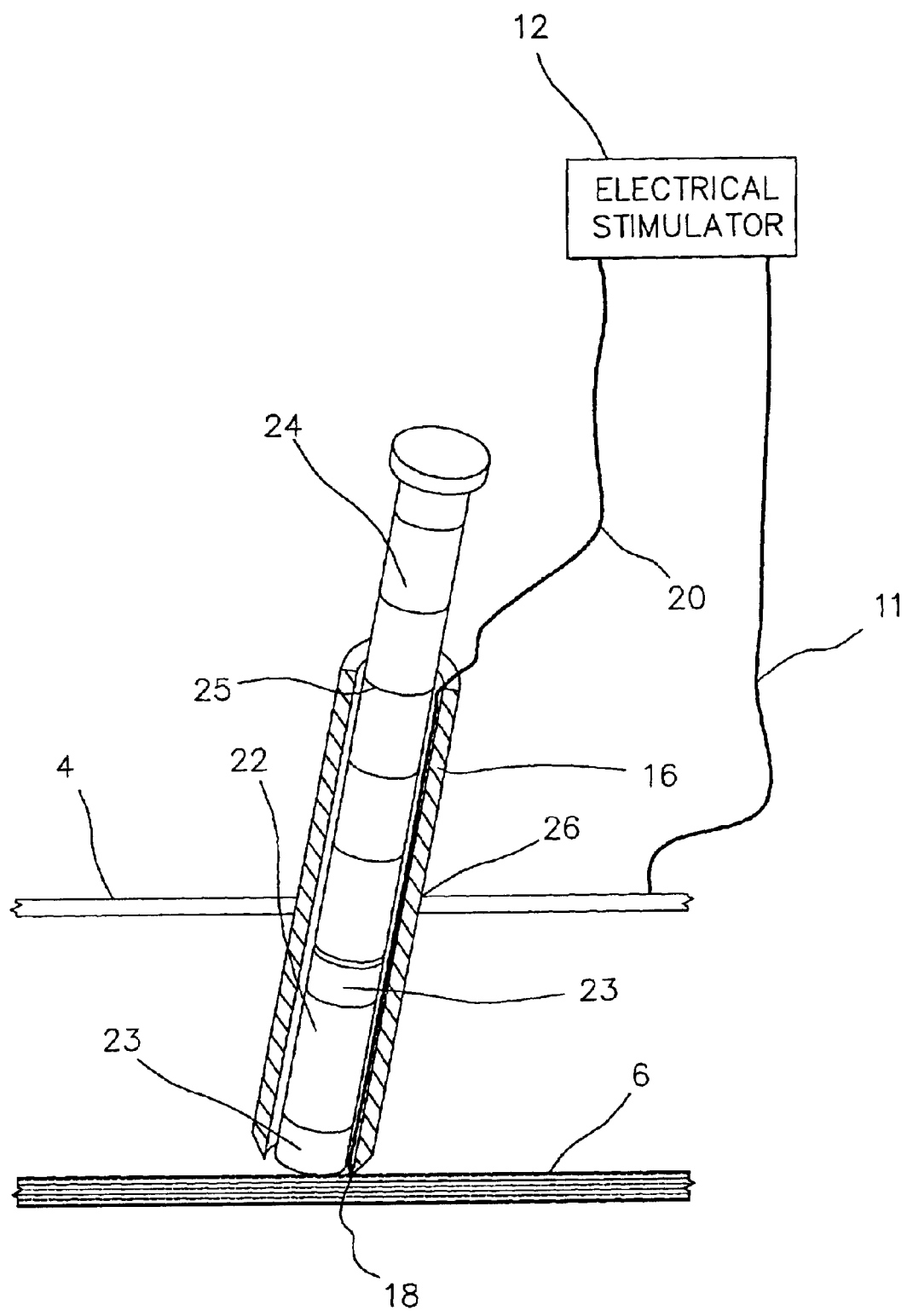
FIG. 4 illustrates a microstimulator in an outer sheath.

Once the electrode probe 2 is removed from the outer sheath 16, FIG. 3, the outer sheath 16 is ready to receive the microstimulator 22 (see FIG. 4). Alternatively as previously discussed, the microstimulator 22 may be a sensor of signals from the living tissue. FIG. 4 illustrates the outer sheath 16 with the microstimulator 22 being pushed into the outer sheath 16 with blunt-end push rod 24. The push rod 24 is inserted to a location mark 25 such that the microstimulator 22 is located at the end of outer sheath 16, near the nerve 6.

Figure 5:
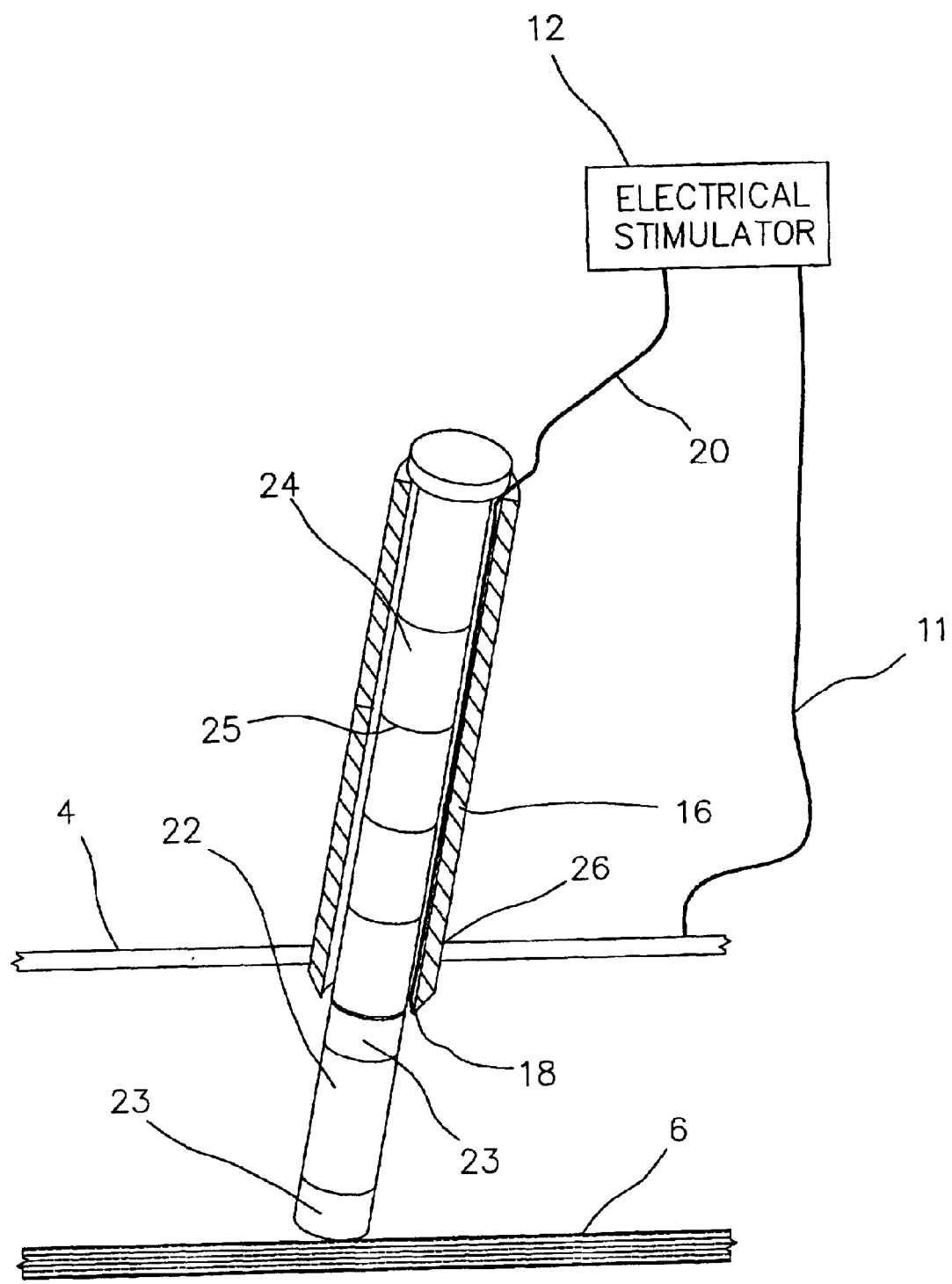
FIG. 5 illustrates a microstimulator as the outer sheath is withdrawn.

The position of the microstimulator 22 can be verified by testing it before the outer sheath 16 is removed. If a problem is discovered, then the microstimulator 22 may be easily removed with the outer sheath 16. If no problem is discovered and if it is desired to implant the microstimulator 22, then the outer sheath 16 is removed, as illustrated in FIG. 5, by holding the microstimulator 22 in position near the nerve 6 with the push rod 24 while the outer sheath 16 is removed.

B. Three-Part System for Placement of a Microstimulator

Figure 6:
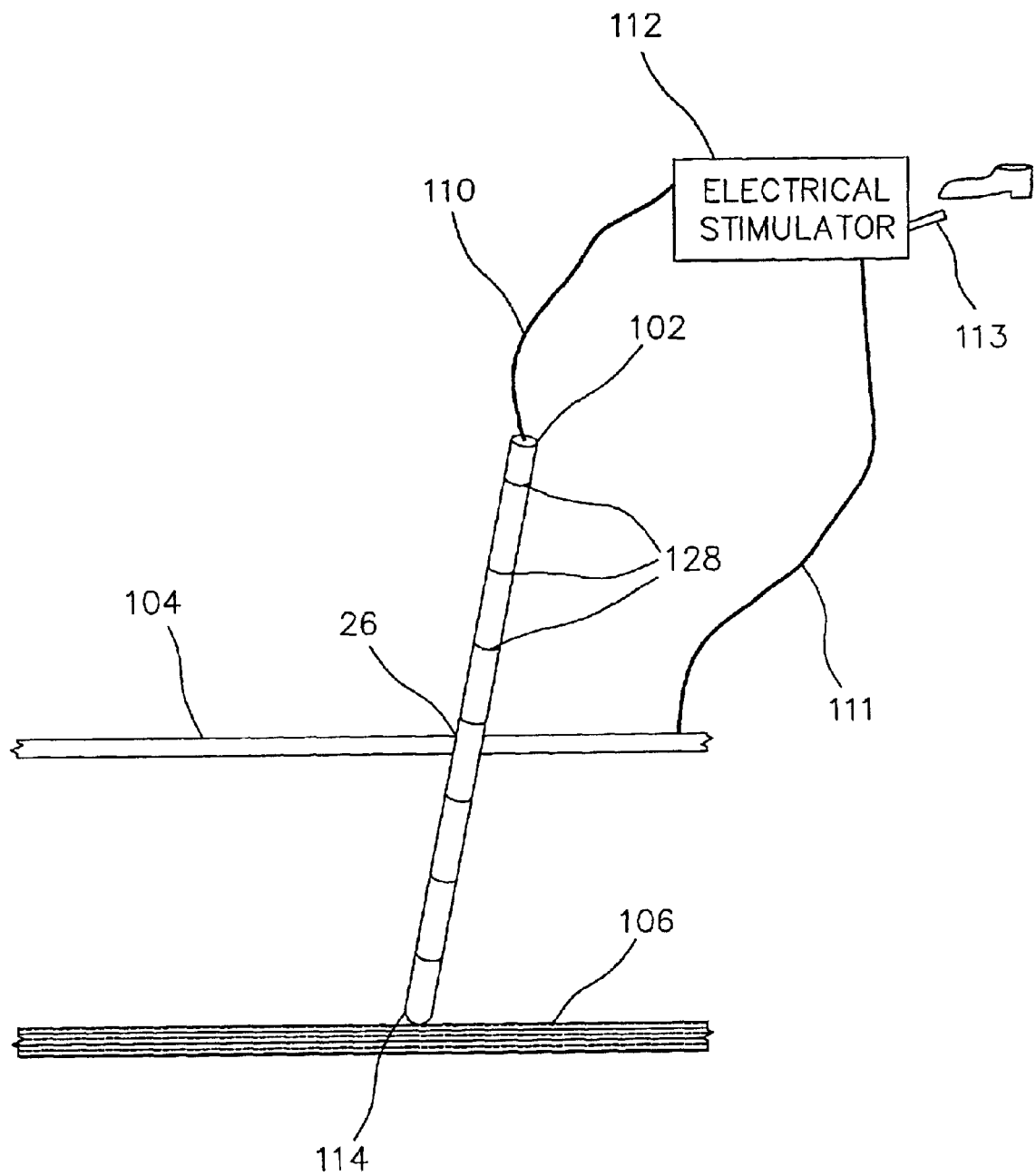
FIG. 6 illustrates a stimulating electrode probe near a nerve.

An alternative embodiment of the invention is illustrated in FIGS. 6–9. FIG. 6 illustrates the electrode probe 102 locating the nerve 106 by electrically stimulating the nerve 106. The response of the associated muscle is observed. Electrode probe 102 is electrically insulated along its length, but conducting tip 114 is not insulated, allowing the electrical signal to pass into the living tissue. The location marks 128 that circumscribe electrode probe 102 provide a precise location of the nerve depth.

The electrical signal is generated by the electrical stimulator 112. The electrical stimulator 112 may be hand-operated or it may be operated by a foot-control lever 113 that is moved by the foot of the surgeon or an assistant. The signal passes along electrode probe wire 110, along electrically insulated electrode probe 102 to conducting tip 114. Return electrode probe wire 111 preferably completes the electrical path by connecting between the skin 4 and electrical stimulator 112.

Figure 7:
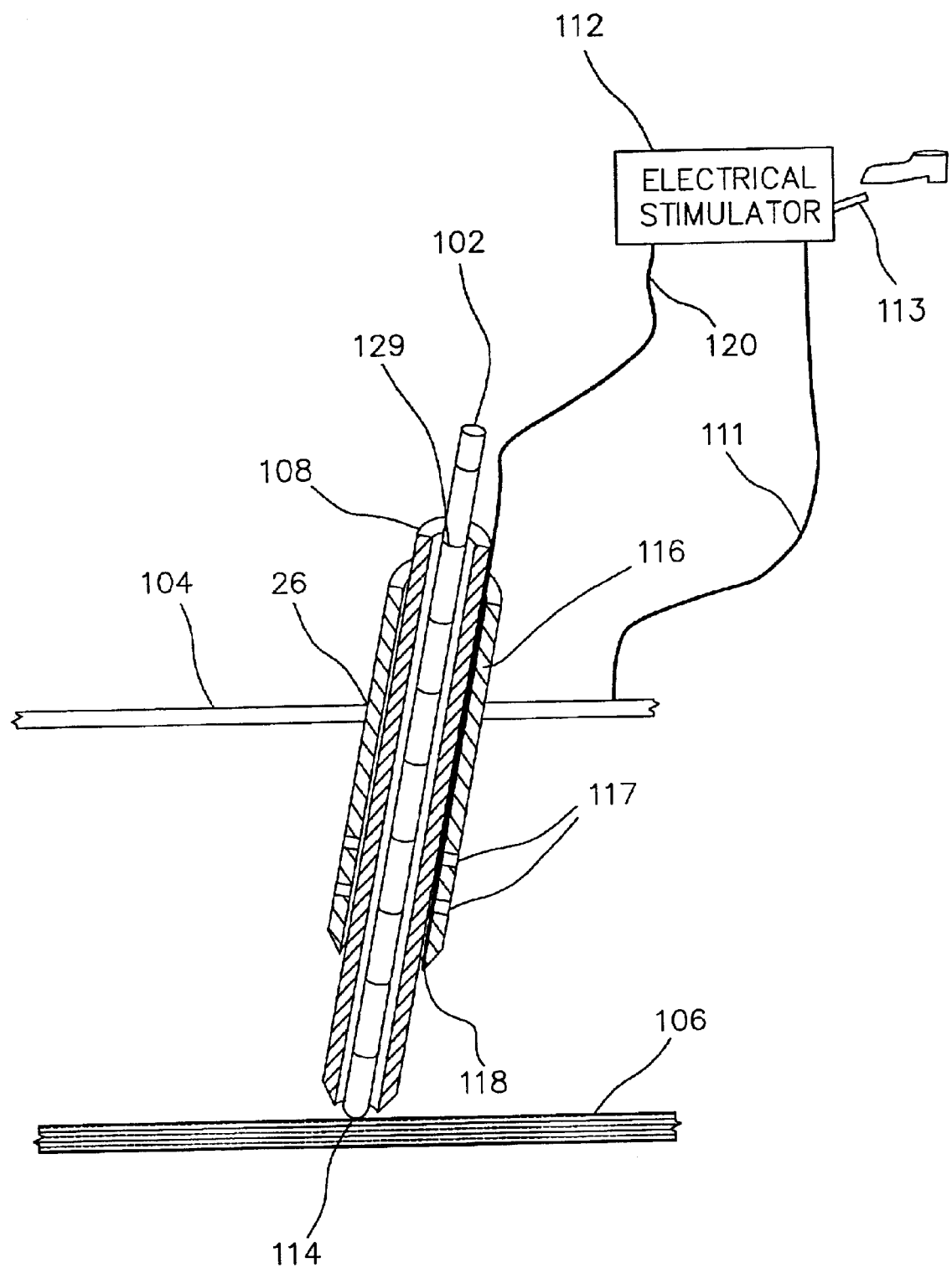
FIG. 7 illustrates a stimulating electrode probe surrounded by an inner sheath and an outer sheath near a nerve.

After the nerve 106 is located, electrode probe wire 110 is detached from the electrode probe 102 (see FIG. 6) and sheath lead wire 120 is attached to sheath electrode 118 (see FIG. 7). Then, an inner sheath 108 and outer sheath 116 are slid along the electrode probe 102, as shown in FIG. 7. The inner sheath 108 is sharp and enters the skin 104 and other living tissue at insertion point 26, enlarging the hole for the implantation, until the top of inner sheath 108 aligns with depth indicator 129 on electrode probe 102 (a selected one of the location marks 128), thereby indicating that the tip of the inner sheath 108 is aligned with and is next to the nerve 106.

The electrode probe 102 is then removed from the inner sheath 108. Next, the inner sheath 108 is removed from the outer sheath 116. The location of the outer sheath 116, with respect to the nerve 106, is determined by passing an electrical signal from the electrical stimulator 112 along electrode probe wire 120, which is preferably embedded in the interior wall of the outer sheath 116, as illustrated in FIG. 7. Alternately, the electrode probe wire 120 may pass along the outside of outer sheath 116 or it may be embedded in the wall of outer sheath 116. Outer sheath 116 is preferably electrically insulated or is comprised of a nonconductive material, such as plastic, to ensure that the electrical pulsing signals that are used to locate the nerve pass into the living tissue and not into the outer sheath 116.

After the electrode probe 102 and the inner sheath 108 have been removed from the outer sheath 116, the outer sheath 116 can no longer be readily relocated because the outer sheath 116 is not designed to penetrate living tissue. Saline solution is injected into outer sheath 116 to ensure that electrical conductivity is established when the microstimulator 122 is placed in outer sheath 116 (see FIG. 8). Outer sheath 116 contains a plurality of holes 117 that are located to facilitate electrical contact between the microstimulator 122 and the living tissue. As described in the incorporated patents, the microstimulator 122 preferably has an axial dimension of less than 60 mm and a lateral dimension of less than 6 mm. In a preferred embodiment, the microstimulator 122 has microstimulator electrodes 123 located on each end. The sheath electrode 118 may be electrically pulsed to ensure that the location of outer sheath 116 has not changed significantly, relative to the nerve 106, while the microstimulator 122 is placed in the outer sheath 116.

Figure 8:
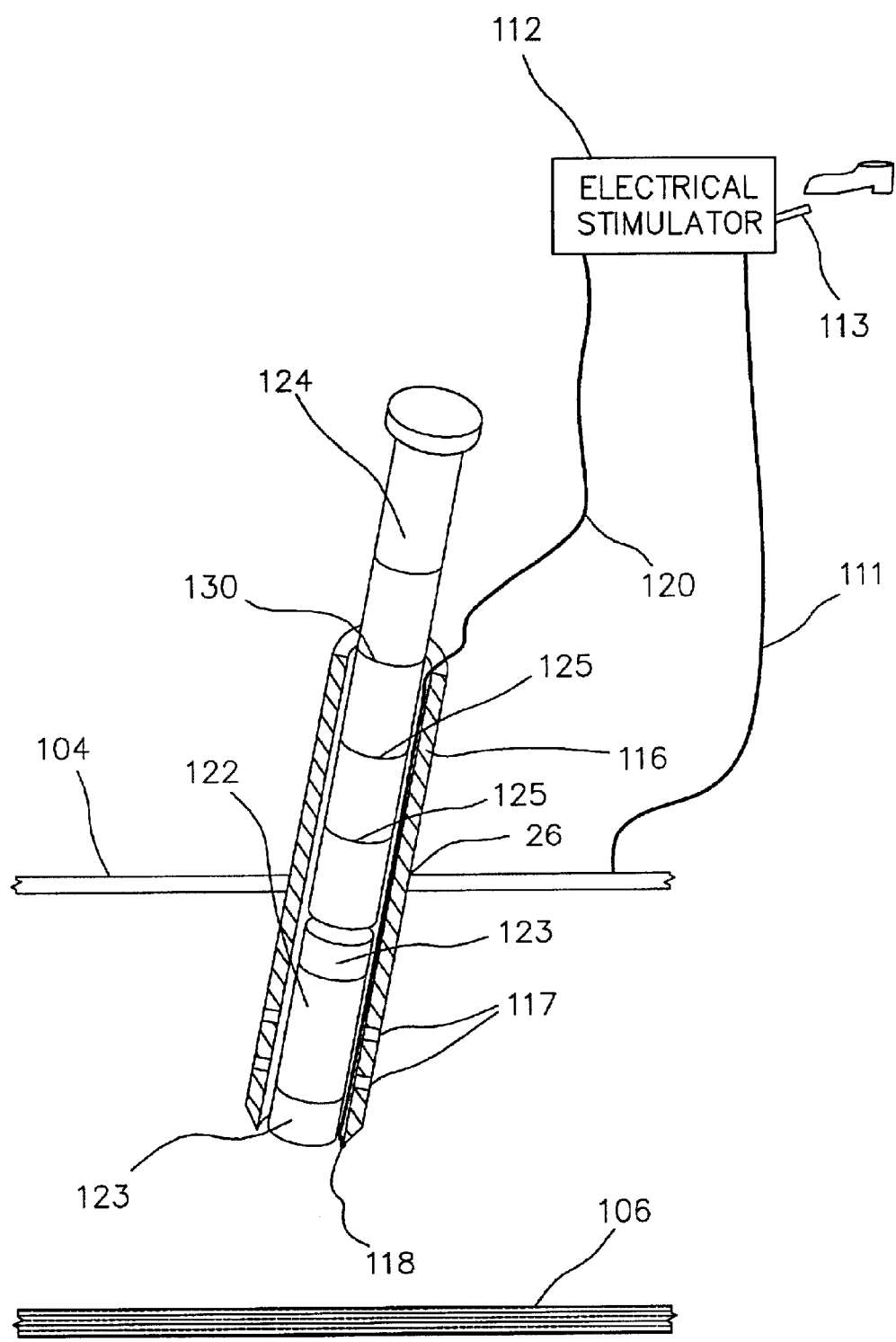
FIG. 8 illustrates an outer sheath with a sheath electrode positioning a microstimulator near a nerve.

FIG. 8 illustrates the microstimulator 122 as it has been placed inside outer sheath 116 and urged toward nerve 106 by blunt-end push rod 124. Blunt-end push rod 124 contains push rod location marks 125, which indicate the position of the microstimulator 122 during insertion. Push rod depth indicator 130 (a selected one of the location marks 125), which indicates when the microstimulator has arrived at the end of outer sheath 116, and is therefore near nerve 106. Alternatively, the microstimulator may be urged along outer sheath 116 by the electrode probe 102 or by inner sheath 108. It is beneficial that any alternative push rod have location marks to indicate when the microstimulator 122 has arrived at the end of the outer sheath 116.

Before the microstimulator 122 is ejected from the outer sheath 116, its position may be confirmed by stimulation of the sheath electrode 118. Furthermore, the function of the microstimulator 122 may be checked by causing stimulation pulses to be emitted from the electrodes of the microstimulator.

Figure 9:
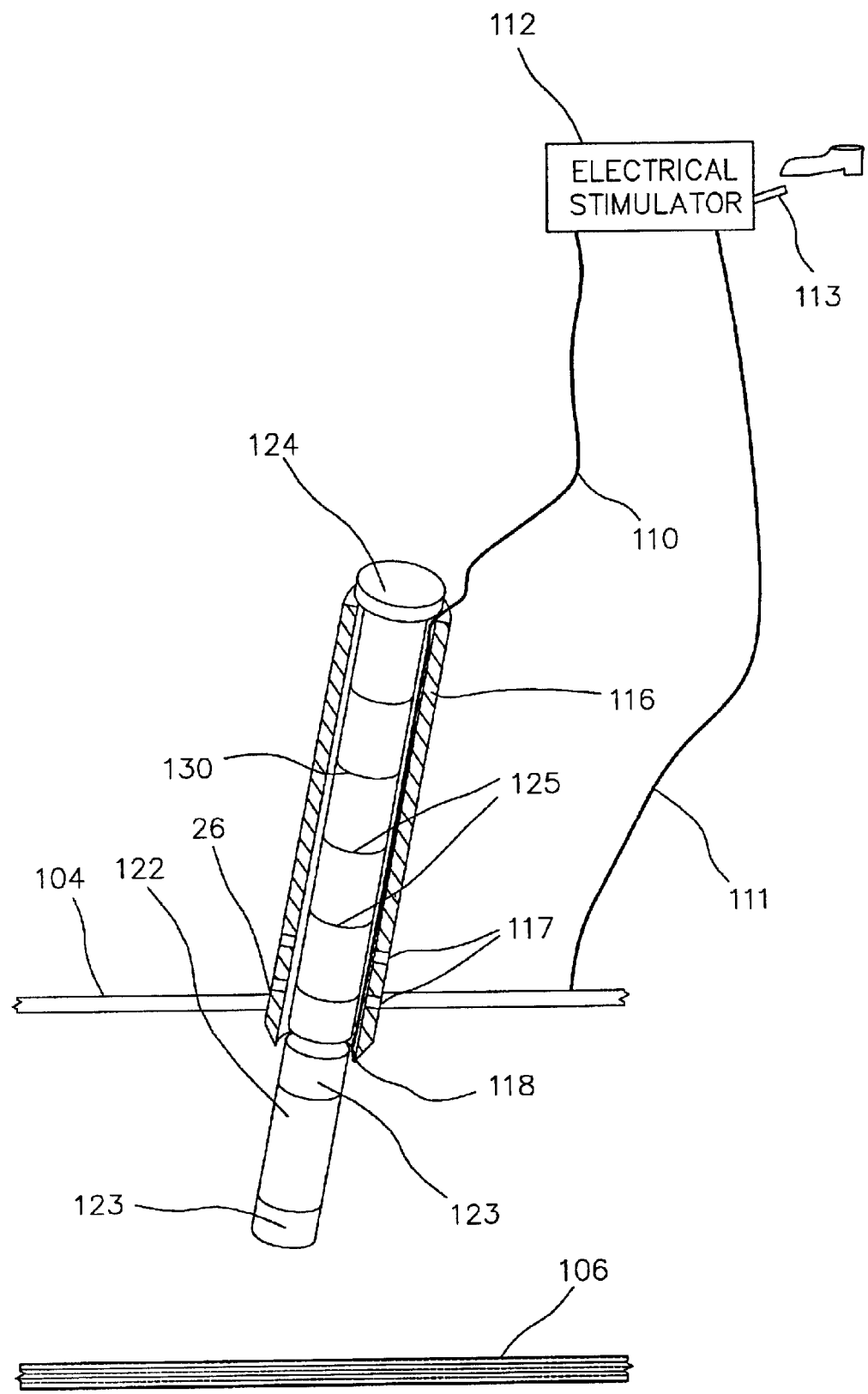
FIG. 9 illustrates an implanted microstimulator after removal of the outer sheath.

Once its position and function are confirmed, the microstimulator 122 is ejected from the outer sheath 116, FIG. 9, by holding the push rod 124 in place as the outer sheath 116 is withdrawn away from the nerve 106 and out of the living tissue at insertion point 26. Typically, this apparatus implants the microstimulator 122 a distance from the nerve 106 that is approximately equal to the distance from the sharp tip of the inner sheath 108 to the tip of outer sheath 116.

C. Improved Three-Part System for Placement of a Microstimulator

Figure 10:
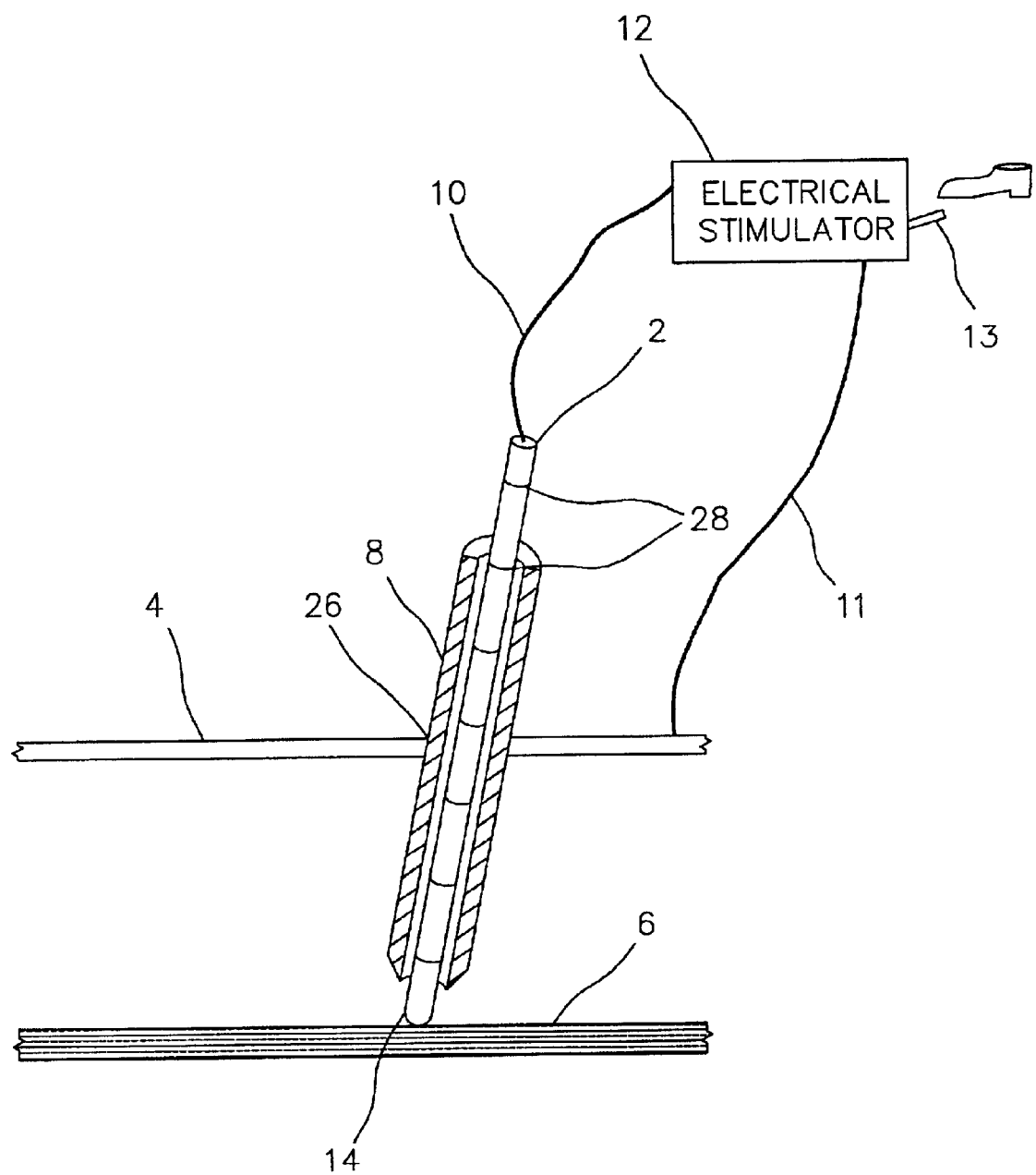
FIG. 10 illustrates an electrode probe surrounded by an inner sheath that is located near a nerve.
Figure 11:
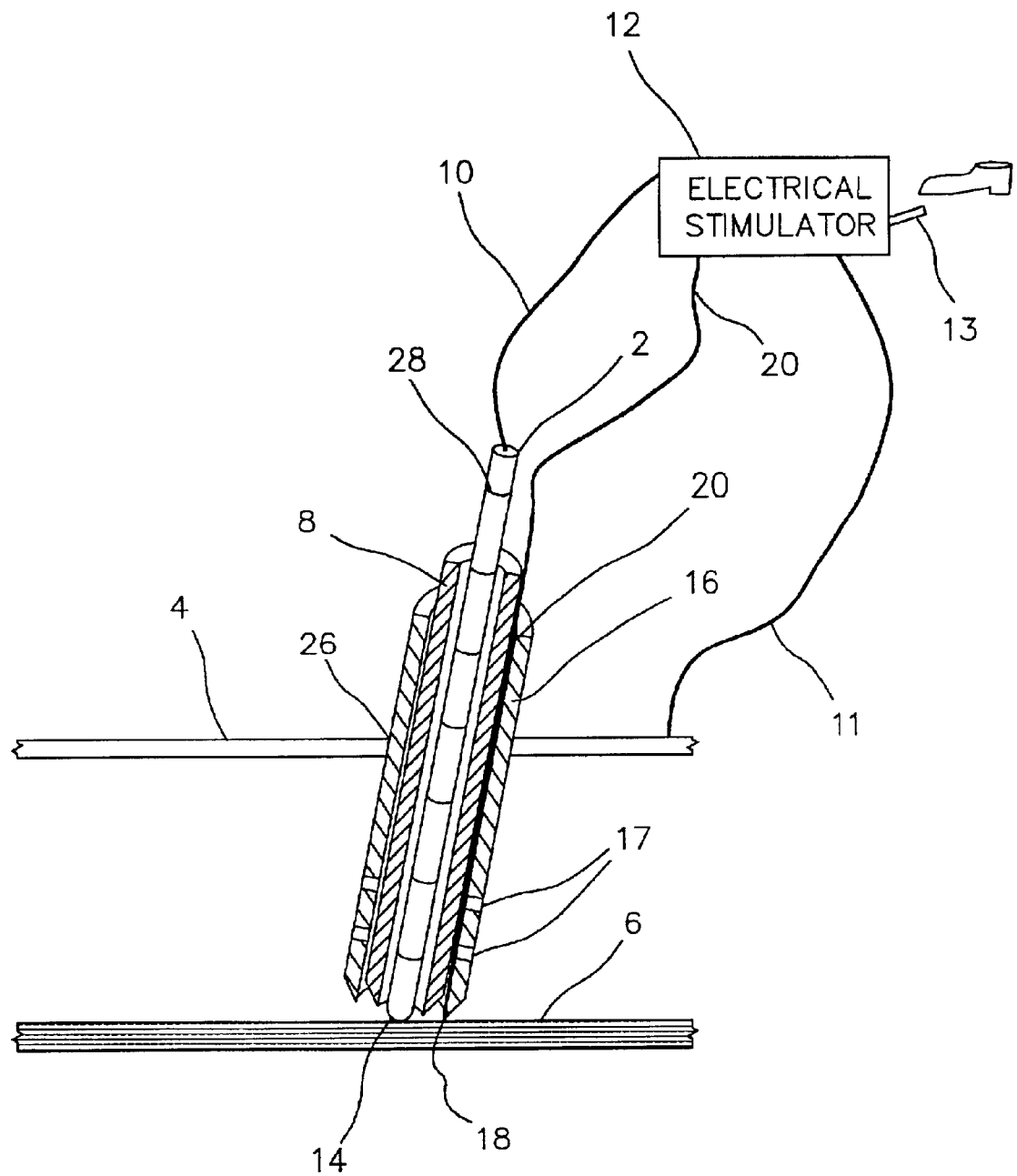
FIG. 11 depicts an electrode probe surrounded by an inner sheath that is surrounded by an outer sheath that is near a nerve.

An alternative embodiment of the invention is presented in FIGS. 10–14. FIG. 10 provides a side view of the electrode probe 2, which is used to initially locate the nerve 6 (and/or muscle tissue) by means of inserting the probe 2 into the living tissue, preferably at an angle to the skin 4 through an insertion point 26 in the skin 4 and into the living tissue. The electrode probe 2 is a sharp device that is electrically insulated along its length but that is not electrically insulated at its conducting tip 14. The electrode probe 2 is used to electrically stimulate the living tissue near the tip 14, thereby locating the desired nerve 6 by eliciting a specific response, such as contraction of a nearby muscle. It is understood that this approach can equally well be used to stimulate muscle tissue.

The electrode probe 2 is attached by electrode probe wire 10 to an electrical stimulator 12, which can be pulsed manually to locate the nerve 6. The electrical path is completed by return electrode probe wire 11, that is preferably attached to skin 4. It is preferred that the electrical stimulator 12 be controlled by foot control 13, although it may be controlled by a hand control in the alternative. The electrode probe 2 location with respect to the nerve 6 and/or the muscle tissue is determined by observing the muscle response when the electrode probe 2 is electrically stimulated. After the electrode probe conducting tip 14 is optimally located, the inner sheath 8 is slid along the electrode probe 2 to enlarge the opening in the tissue (see FIG. 10). In an alternative embodiment, the inner sheath 8 and outer sheath 16 may be simultaneously slid along the pre-positioned electrode probe 2 into the living tissue.

In a preferred embodiment (see FIG. 11), the electrode probe 2 is held in close proximity to the nerve 6 while a cylindrically hollow outer sheath 16 is slid over the inner sheath 8. The inside diameter of inner sheath 8 has a diametral dimension that is preferably slightly larger than the outer diameter of electrode probe 2, e.g., by 5% to 20%, while the outside diameter of inner sheath 8 preferably is approximately equal to the outside diameter of microstimulator 22, e.g., within about 5% (see FIG. 13). A thin electrically conductive sheath lead wire 20, having a diameter of about one-thousandth of an inch, is located in the wall of outer sheath 16 connecting the sheath electrode 18 and the electrical stimulator 12. The sheath electrode 18 is located on the end of the outer sheath 16 that is nearest the nerve 6.

This device offers the additional improved feature that both the outer sheath 16 and the inner sheath 8 are near the nerve 6, thus allowing the ultimate position of the implanted microdevice to be near the nerve 6. The closer the implanted microdevice is to the nerve, generally, the less power is consumed in its operation and the longer the device will survive without battery replacement.

Figure 12:
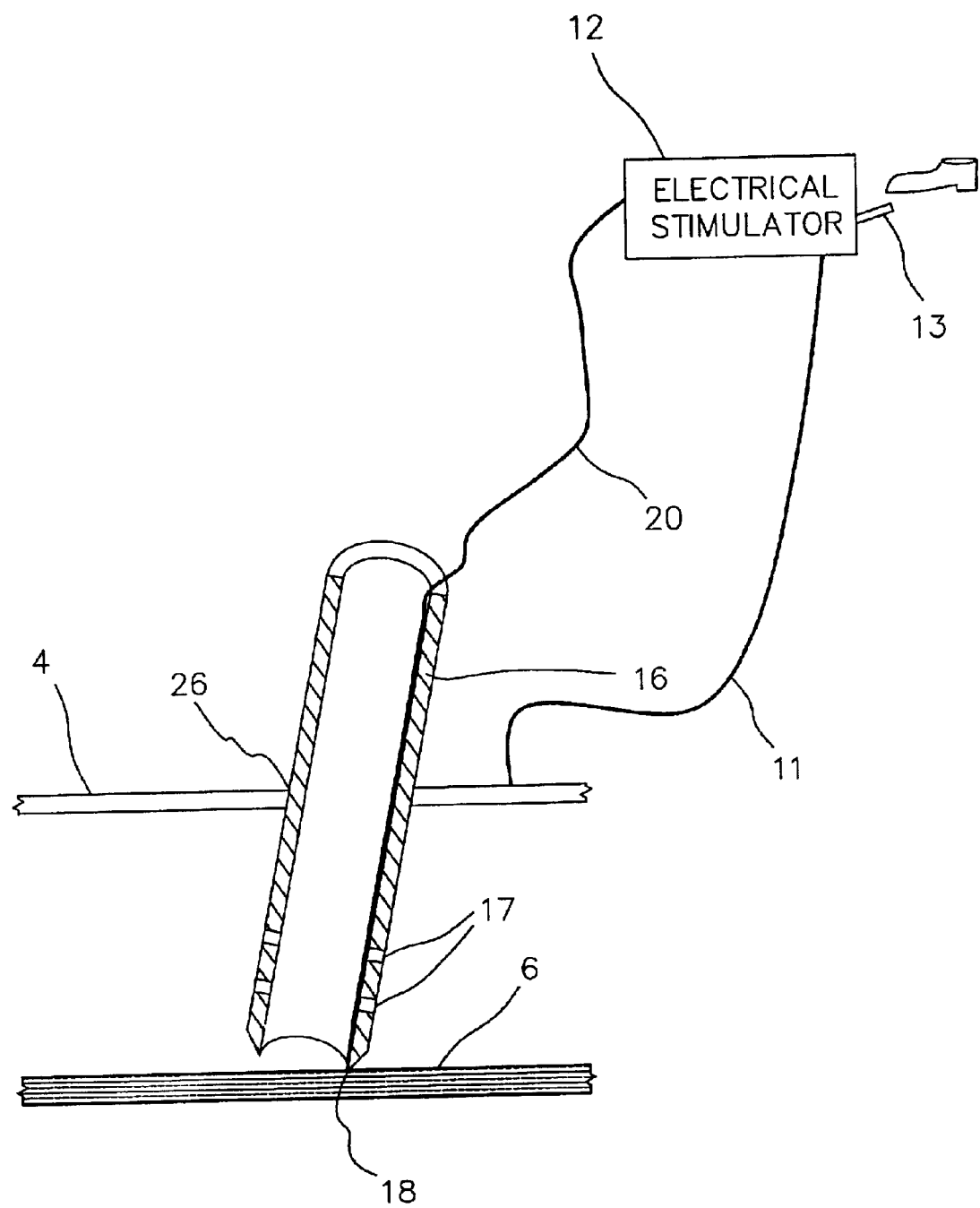
FIG. 12 depicts an outer sheath and sheath electrode near a nerve.

As shown in FIG. 12, the electrode probe 2 and inner sheath 8 are removed from the living tissue while the position of the outer sheath 16 is maintained next to the nerve 6 by electrically pulsing the nerve 6 with a current from sheath electrode 18 and observing the response of the muscle associated with the nerve 6. In order to ensure that there is no interference with electrical stimulation of the nerve 6, both the inner sheath 8 and the outer sheath 16 must be non-conductors or must be electrically insulated from the living tissue. Accordingly, in a preferred embodiment, the inner sheath 8 and the outer sheath 16 are made of plastic.

The sheath lead wire 20 may be located in alternative locations in or along the wall of the outer sheath 16. The sheath lead wire 20 may be located in the wall, which is preferred, or along the outside of the hollow outer sheath 16, or inside the outer sheath 16, e.g., in a groove. The sheath lead wire 20 can then be used to conduct an electrical signal to stimulate the nerve 6 and to confirm the position of the outer sheath 16 relative to the nerve 6.

Prior to insertion of the microstimulator 22, the outer sheath 16 may be flushed with saline solution. Holes 17 are located in the outer sheath at locations to ensure good electrical contact between the microstimulator 22, after it is inserted into the outer sheath 16, and the living tissue.

A microstimulator 22 (see FIG. 13) is typically a small tubular device that contains an electronic package and communication means, for modifying or affecting a body parameter, when it is located near a nerve 6 or muscle to be stimulated. In a preferred embodiment, the microstimulator 22 has microstimulator electrodes 23 located on each end.

Figure 13:
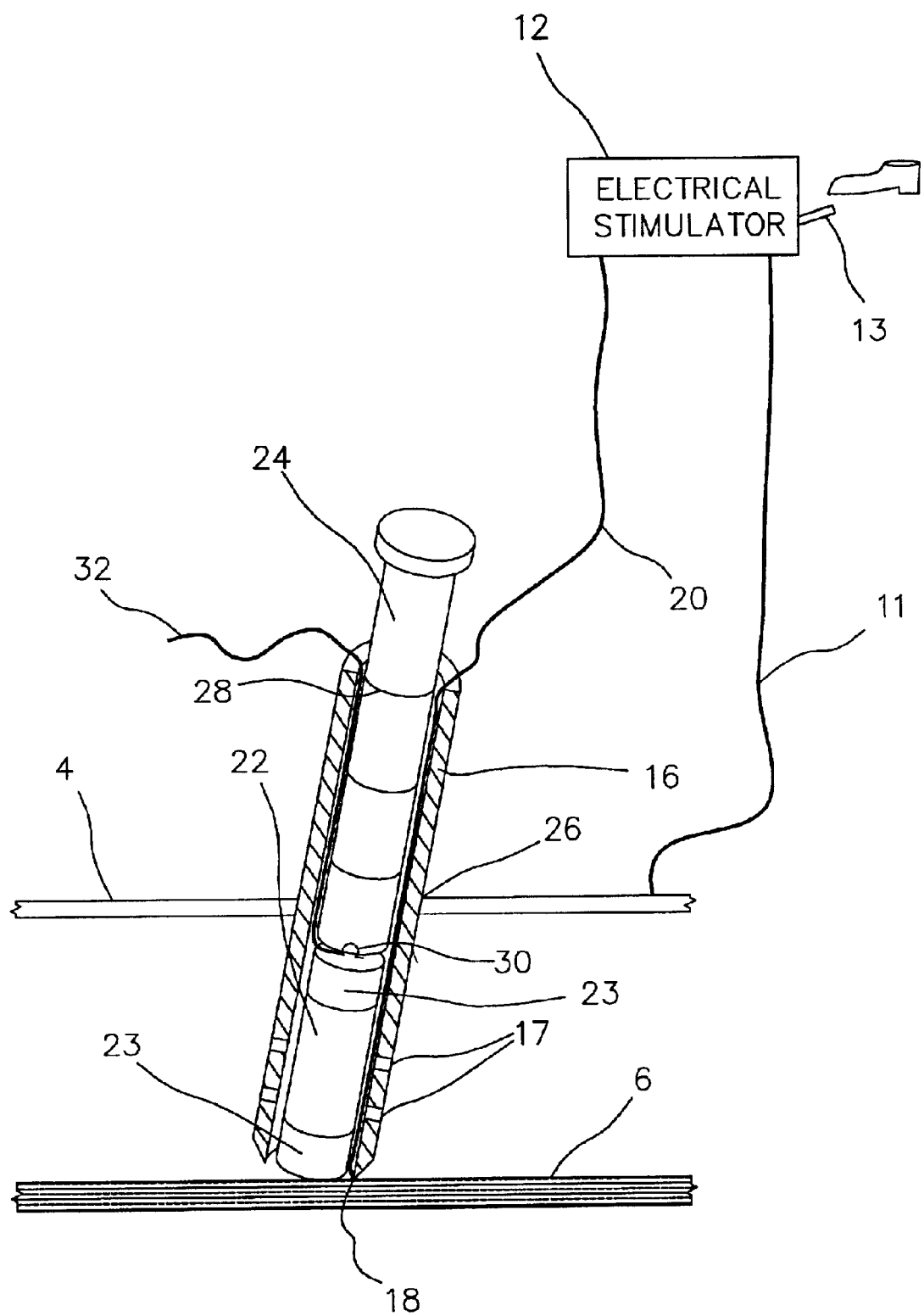
FIG. 13 depicts an outer sheath and sheath electrode near a nerve with a microstimulator being inserted by a blunt-end push rod.

FIG. 13 illustrates the microstimulator 22 being inserted into the outer sheath 16 using the blunt-end push rod 24. Alternately, the microstimulator can be inserted into the outer sheath 16 by using the electrode probe 2 or inner sheath 8. The blunt-end push rod 24 has location mark 28 that circumscribes the push rod 24 such that the location of the microstimulator 22 in the outer sheath 16 can be ascertained by reference to the location mark 28.

Figure 14:
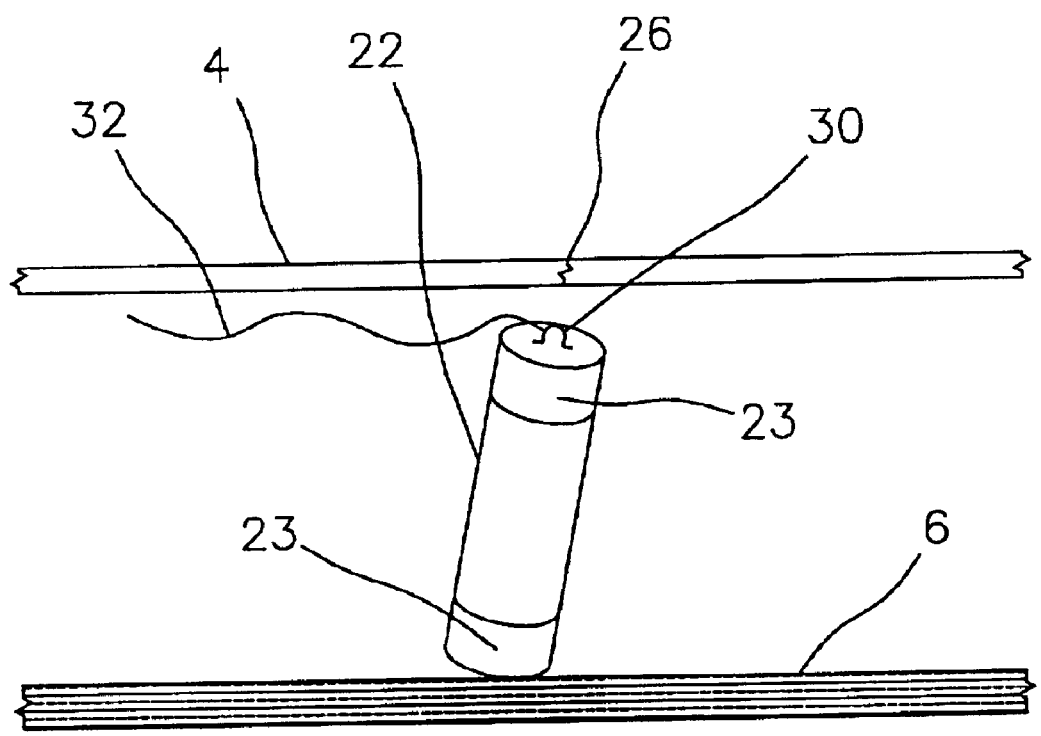
FIG. 14 depicts an implanted microstimulator near a nerve.

Once the microstimulator 22 is placed in contact with the nerve 6, by passing the microstimulator 22 down the length of the inner sheath 8, the microstimulator 22 is activated and powered via an externally provided RF signal and the muscle that responded before is observed to see if it is still responding when stimulated by the microstimulator 22. In an alternative embodiment, the microstimulator 22 may be activated by an RF signal or powered by means other than via an RF signal, such as by an internal battery. If the muscle is responding properly, the outer sheath 16 is pulled back while restraining the microstimulator 22 with the blunt-end push rod 24 (see FIG. 13). The microstimulator 22 is free of the outer sheath 16 and both the outer sheath 16 and blunt-end push rod 24 are removed from the living tissue. The microstimulator 22 remains in position next to the nerve 6 and at the base of insertion point 26, as illustrated in FIG. 14, after the outer sheath 16 and the blunt-end push rod 24 have been removed.

D. Removal of a Microstimulator with a String Loop

In a preferred embodiment, the microstimulator 22 (see FIG. 13) contains removal loop 30, e.g., an eyelet, on the end nearest the skin 4 to facilitate attachment of removal string 32 to the microstimulator 22. The removal string 32 may be left in the living tissue near the insertion point 26 (see FIG. 14) or it may be left outside the living tissue. The removal string may be used to locate and/or to remove the microstimulator by pulling on it. This technique is effective for a few days post-surgery to remove the microstimulator 22 without risking further damage or trauma to the implant area, until the tissue begins to heal and adheres to the microstimulator.

E. Removal of a Microstimulator with a Fabric Sock

Figure 15:
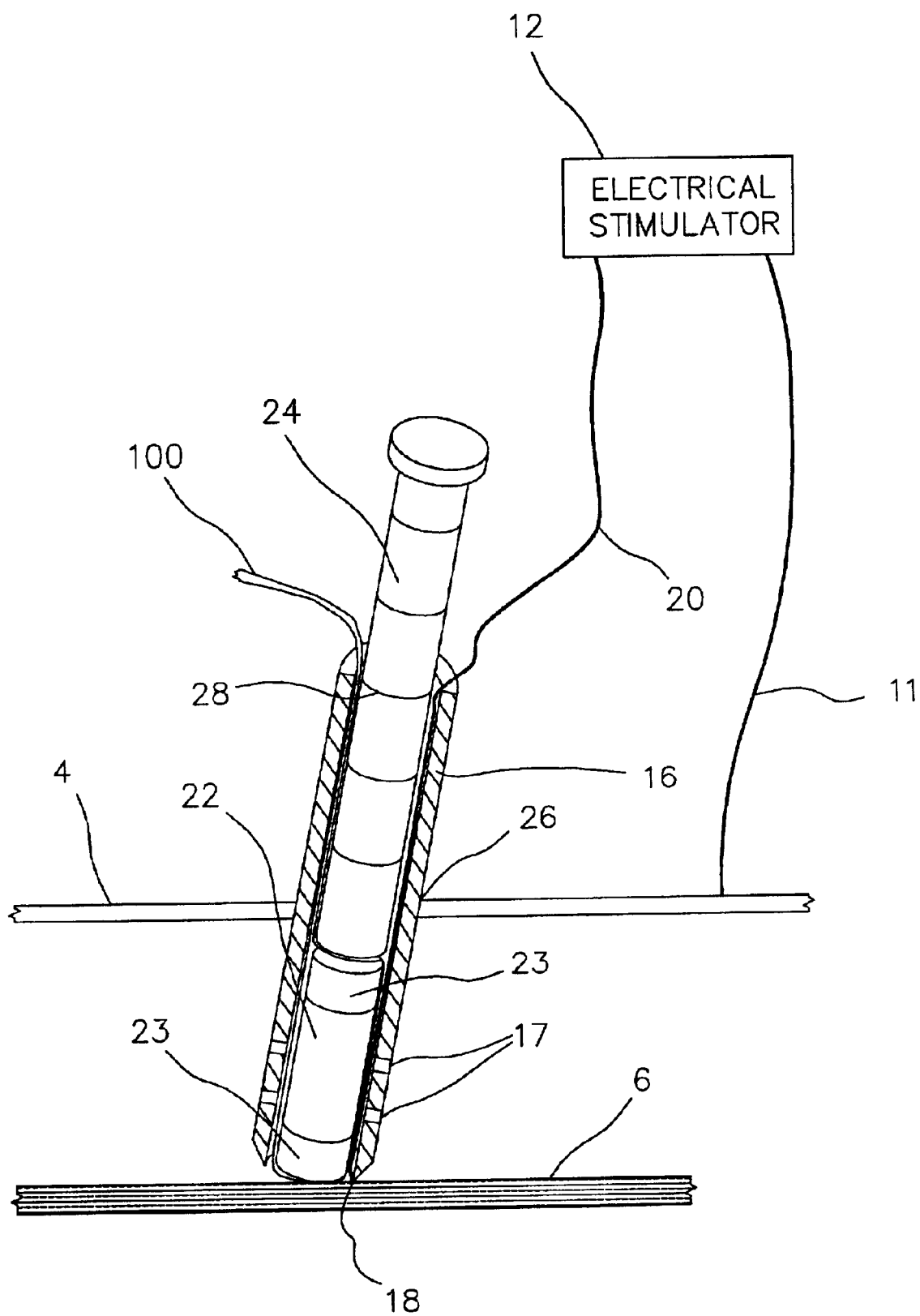
FIG. 15 illustrates an outer sheath and sheath electrode near a nerve with a microstimulator that is contained in a silk tube being inserted by a blunt-end push rod.

An alternative embodiment to the removal system using the removal string 32 connected to the removal loop 30 on the microstimulator 22 (see FIGS. 13 and 14) is to place the microstimulator 22 in a porous, non-soluble, biocompatible fabric tube 100 (see FIG. 15). A preferred material for biocompatible fabric tube 100 is a silk tube, which is essentially a "sock" or closed end tube. Silk is a preferred material because it is biocompatible and does not bond readily to the living tissue. As an alternative to silk, any closely woven material made of non-soluble material may be used. Alternatives include dialysis membrane materials. The ideal material is porous to allow solute materials to penetrate and flood the microstimulator surfaces for optimum electrical contact, however the structure of the materials must be so fine that the body's connective tissue cannot penetrate and lock the fabric tube 100 into place. Should the microstimulator 22 need to be removed, then the end of the fabric tube 100 is located either protruding from the skin 4 or implanted beneath the skin 4 near insertion point 26, and slowly withdrawn from the living tissue with the microstimulator 22 inside.

F. Two-Part System with Expanding Aperture for Placement of a Microstimulator A further embodiment of an insertion system for placing a microstimulator or microsensor into living tissue is presented in FIGS. 16–18. In an analogous process to that previously discussed the electrically insulated electrode probe 202 is first inserted in the living tissue through the skin 204 at insertion point 26 in order to locate a nerve 206 by electrically stimulating the nerve 206 and visually observing the muscle response. The electrical signal is generated by an electrical stimulator 212 and the signal passes along a wire (not illustrated) to the electrode probe 202 and to the exposed electrically conductive tip 214 of the electrode probe 202. The circuit is completed by return electrode probe wire 211 that is preferably attached to the skin 204.

The insulated wire 210 is removed from the electrode probe 202 after the probe 202 has located the nerve 206.

Figure 16:
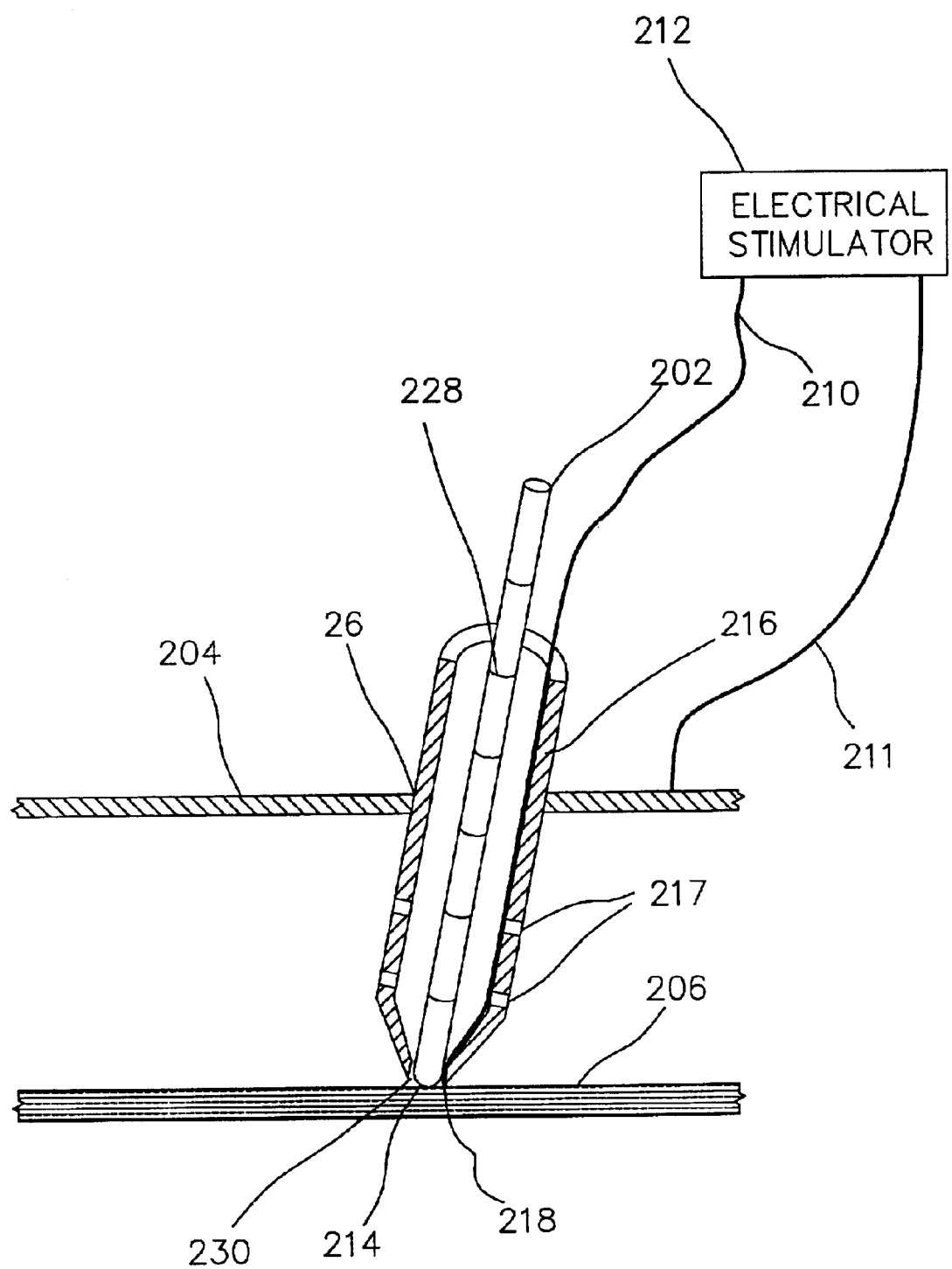
FIG. 16 illustrates an electrode probe with a dilator outer sheath and sheath electrode positioned near a nerve.

As illustrated in FIG. 16, the dilator outer sheath 216 is inserted over electrode probe 202 and into the living tissue until the aperture tip 230 of the dilator outer sheath 216 is approximately aligned with the conducting tip 214 of the electrode probe 202. The dilator outer sheath 216 has a sharp end to facilitate insertion into the living tissue. The sharp end forms aperture 230.

The proper alignment is achieved by visually aligning the dilator outer sheath 216 with the location mark 228. The electrode probe 202 is removed and the location, relative to the nerve 206, of the dilator outer sheath 216 is confirmed by passing an electrical signal from the electrical stimulator 212 along the electrically insulated wire 210, which in a preferred embodiment extends along the inside wall of the dilator outer sheath 216. The insulated wire 210 terminates in sheath electrode 218, which is located near aperture 230. The circuit is completed by return electrode probe wire 211 that is preferably attached to the skin 204.

In alternative embodiments, the wire 210 may be located along the outside wall or may be replaced with a conductive path along the outside wall of the dilator outer sheath 216 or along the inside wall of the dilator outer sheath 216. The nerve 206 is pulsed with an electrical signal from the sheath electrode 218 and the response of the muscle is observed.

Preferably, the dilator outer sheath 216 is electrically insulated to avoid conduction of electricity into the dilator outer sheath 216 and away from nerve 206. The dilator outer sheath 216 is preferably comprised of plastic. Dilator outer sheath 216 preferably contains a plurality of holes 217 that pass through the wall near the aperture 230 (see FIG. 17). The holes 217 are preferably located to provide an electrically conductive path between the living tissue and the microstimulator 222.

Figure 17:
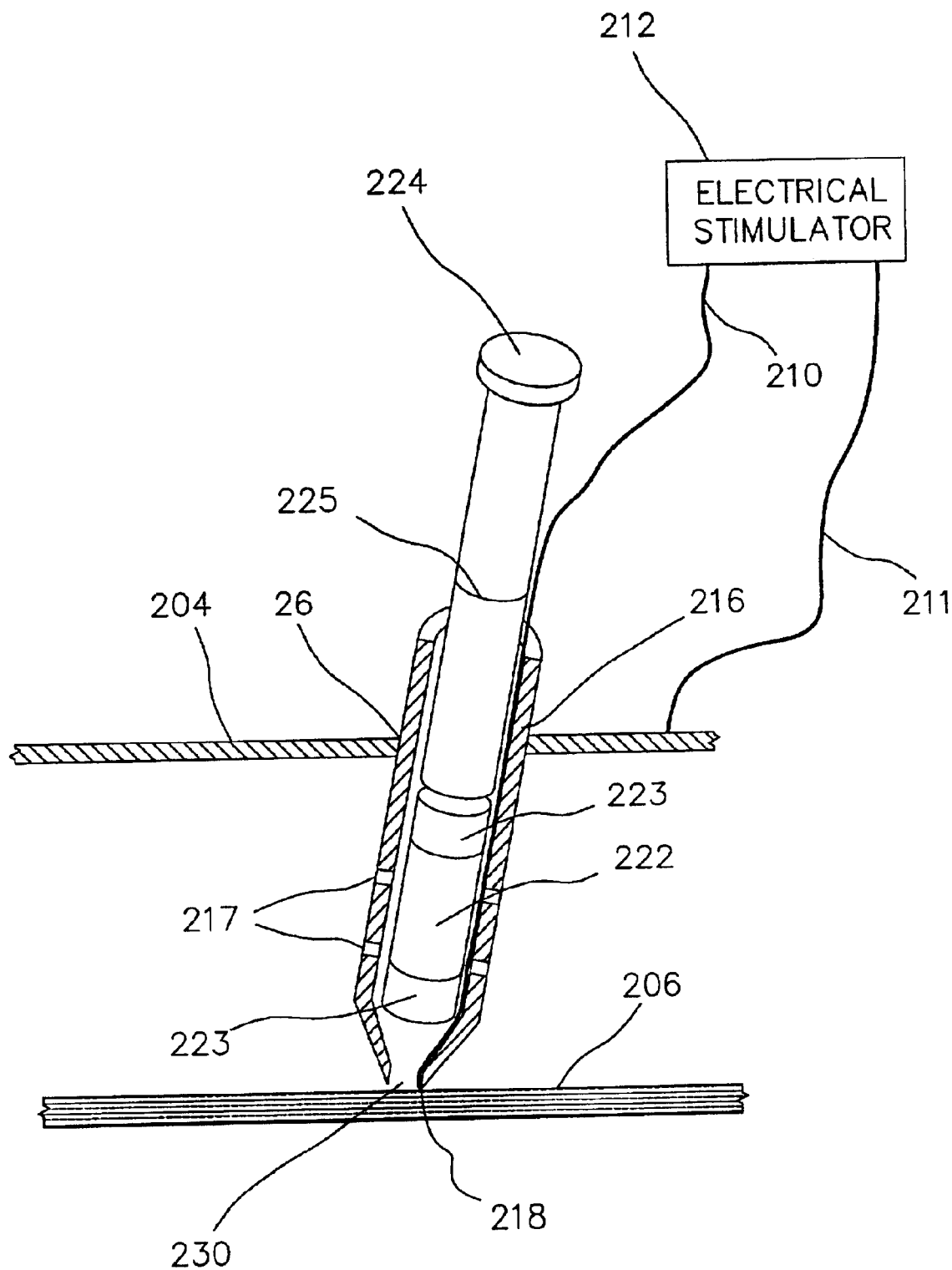
FIG. 17 illustrates a dilator outer sheath with a sheath electrode containing a microstimulator for placement near a nerve.

FIG. 17 illustrates the dilator outer sheath 216 with the microstimulator 222 inserted therein and next to the aperture 230 that is next to the nerve 206. The microstimulator 222 is shown inserted part way along the inside of the dilator outer sheath 216 in FIG. 17.

In a preferred embodiment (see FIG. 17), the microstimulator 222 has microstimulator electrodes 223 located on each end. The microstimulator 222 will be inserted until the nerve-end of the microstimulator 222 is approximately even with the aperture 230 formed by dilator outer sheath 216. When the microstimulator 222 is fully inserted in dilator outer sheath 216, the microstimulator 222 is near nerve 206. The inside diameter of the dilator outer sheath 216 is preferably larger than the outside diameter of the microstimulator 222, e.g., by 5% to 20%, allowing the microstimulator 222 to pass along the length of the dilator outer sheath 216 with moderate pressure from the blunt-end push rod 224. In a preferred embodiment, the microstimulator 222 is positioned by using the blunt-end push rod 224, although the electrode probe 202 or another comparable probe with location marks can be used.

Since the dilator outer sheath 216 may move after electrode probe 202 is removed and during the insertion of microstimulator 222, the location of the dilator outer sheath 216, and more particularly the aperture 230, next to the nerve 206 is verified by preferably pulsing nerve 206 with a current from conducting tip 218 and observing the response of the muscle.

Prior to removing dilator outer sheath 216 and leaving the microstimulator 222 implanted next to nerve 206, the function of the microstimulator 222 is confirmed by checking its electrical functions. If there is a problem with the microstimulator 222 or if the dilator outer sheath 216 moved and is no longer located next to the nerve 206, then the microstimulator 222 may be removed by withdrawing the dilator outer sheath 216 from the living tissue.

Figure 18:
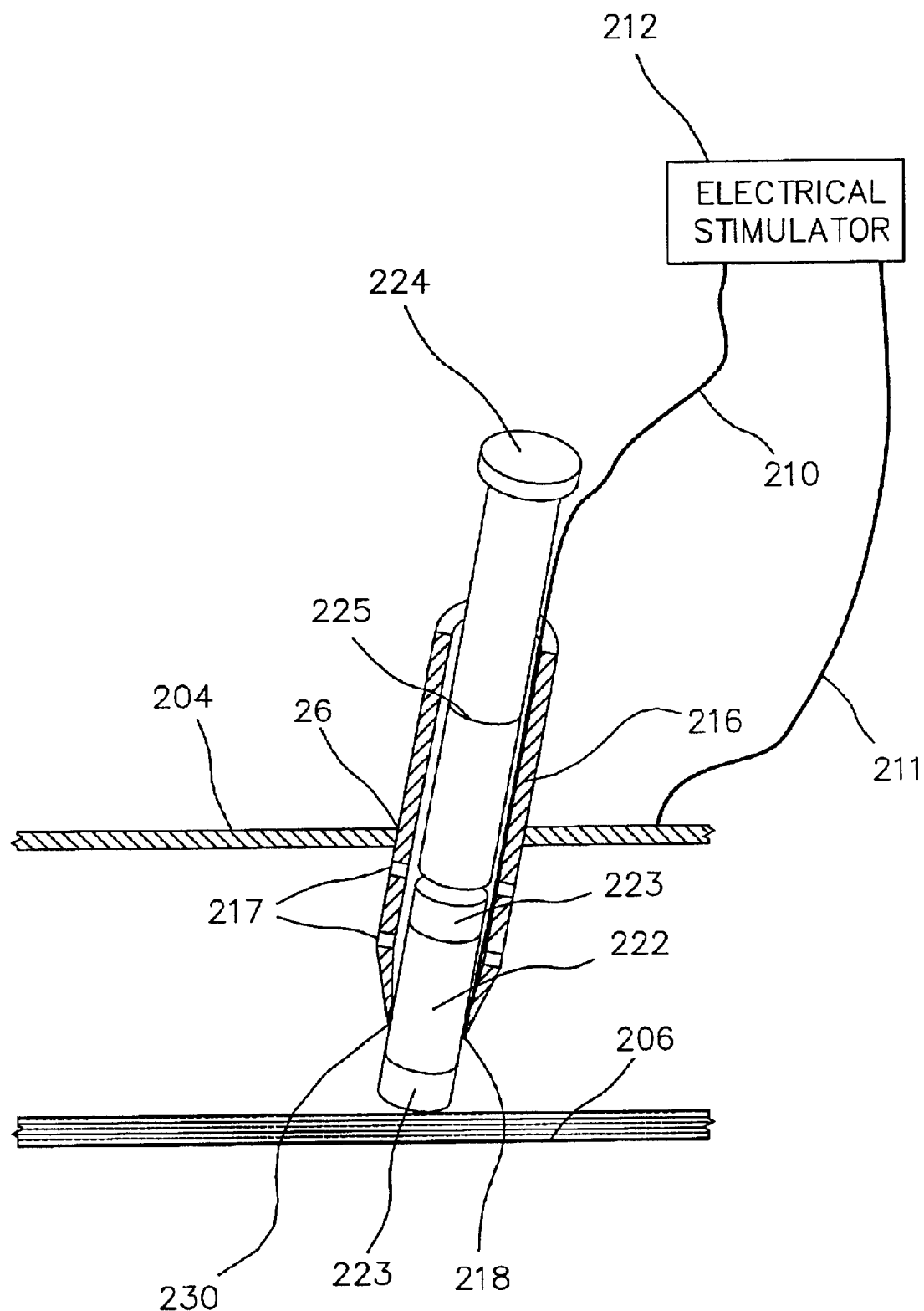
FIG. 18 illustrates a microstimulator being ejected from a dilator outer sheath near a nerve.

If it is desired to implant the microstimulator 222, then the dilator outer sheath 216 is removed from the living tissue by holding the microstimulator 222 in place with the blunt-end push rod 224 and moving the dilator outer sheath 216 along the push rod 224 and out of the living tissue (see FIG. 18). Aperture 230 enlarges as microstimulator 222 is forced through the aperture.

The microstimulator 222, shown in FIG. 18, has been partially ejected from dilator outer sheath 216. The aperture 230 expandably conforms to the outside diameter of microstimulator 222 during the ejection process. In a preferred embodiment, the dilator outer sheath 216 is comprised of an electrical insulator, such as plastic, that conforms to allow ejection of the microstimulator 222. The microstimulator 222 is completely ejected by removing the dilator outer sheath 216 from the living tissue and leaving the microstimulator 222 in place next to the nerve 206.

G. Device for One-Handed Placement of a Microstimulator

Figure 19:
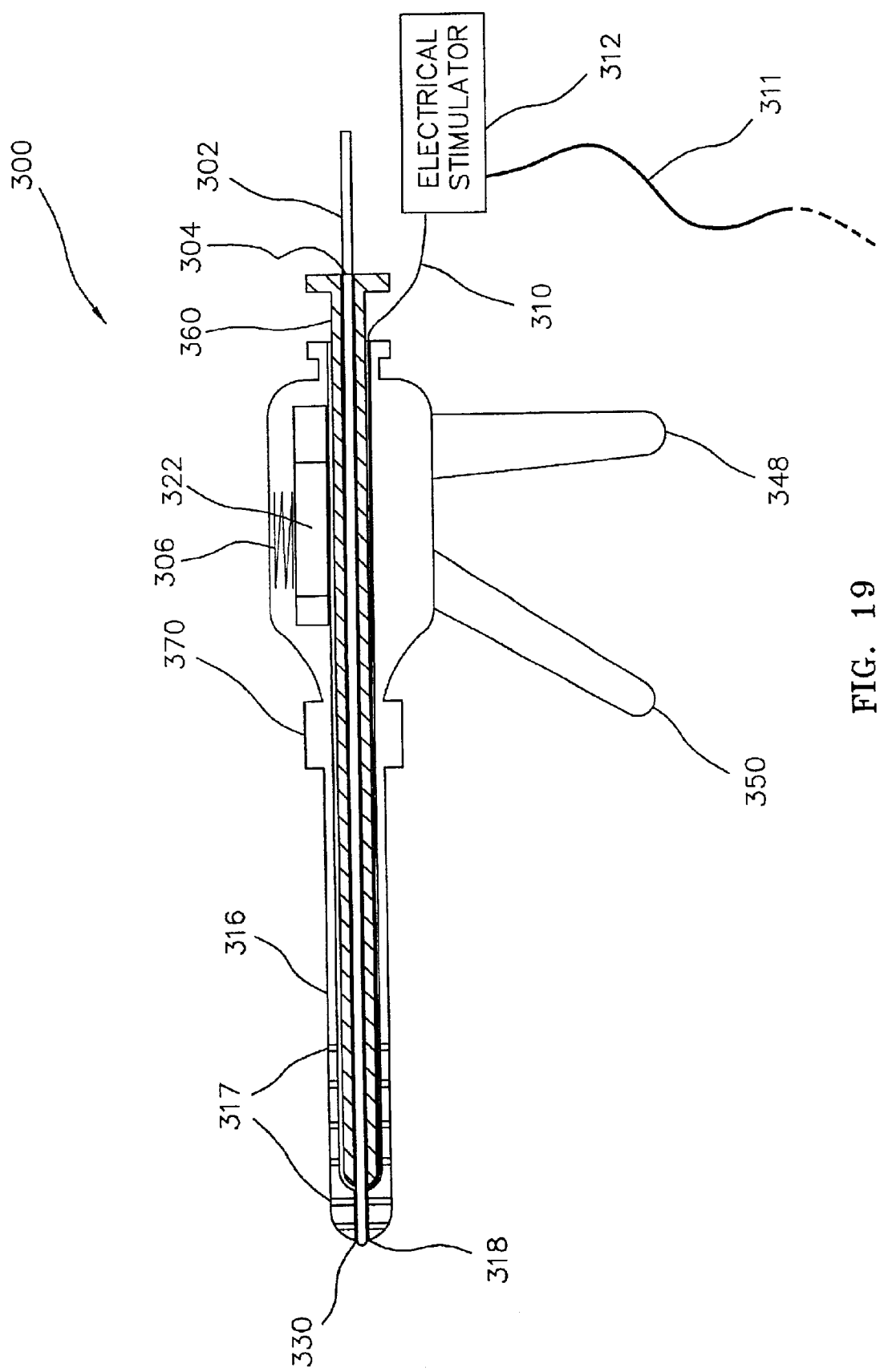
FIG. 19 illustrates a microstimulator ejection tool.

Placement of a microstimulator 322 in living tissue may be facilitated by using the implantation tool 300 of FIG. 19. This implantation tool 300 enables one-handed placement of a microstimulator 322 near a nerve (not illustrated). The procedure begins with electrode probe 302 being used to locate the desired nerve by using electrical stimulation, as previously described. Electrode probe 302 is electrically insulated along its length to eliminate electrical shorts and is electrically conductive at its tip to pass an electrical signal to the stimulating site near the nerve. The implantation tool 300 is then slid over electrode probe 302. The electrode probe 302 is held steady until the aperture 330 is next to the nerve, as determined by observing the mark 304 on the electrode probe 302.

Figure 20:
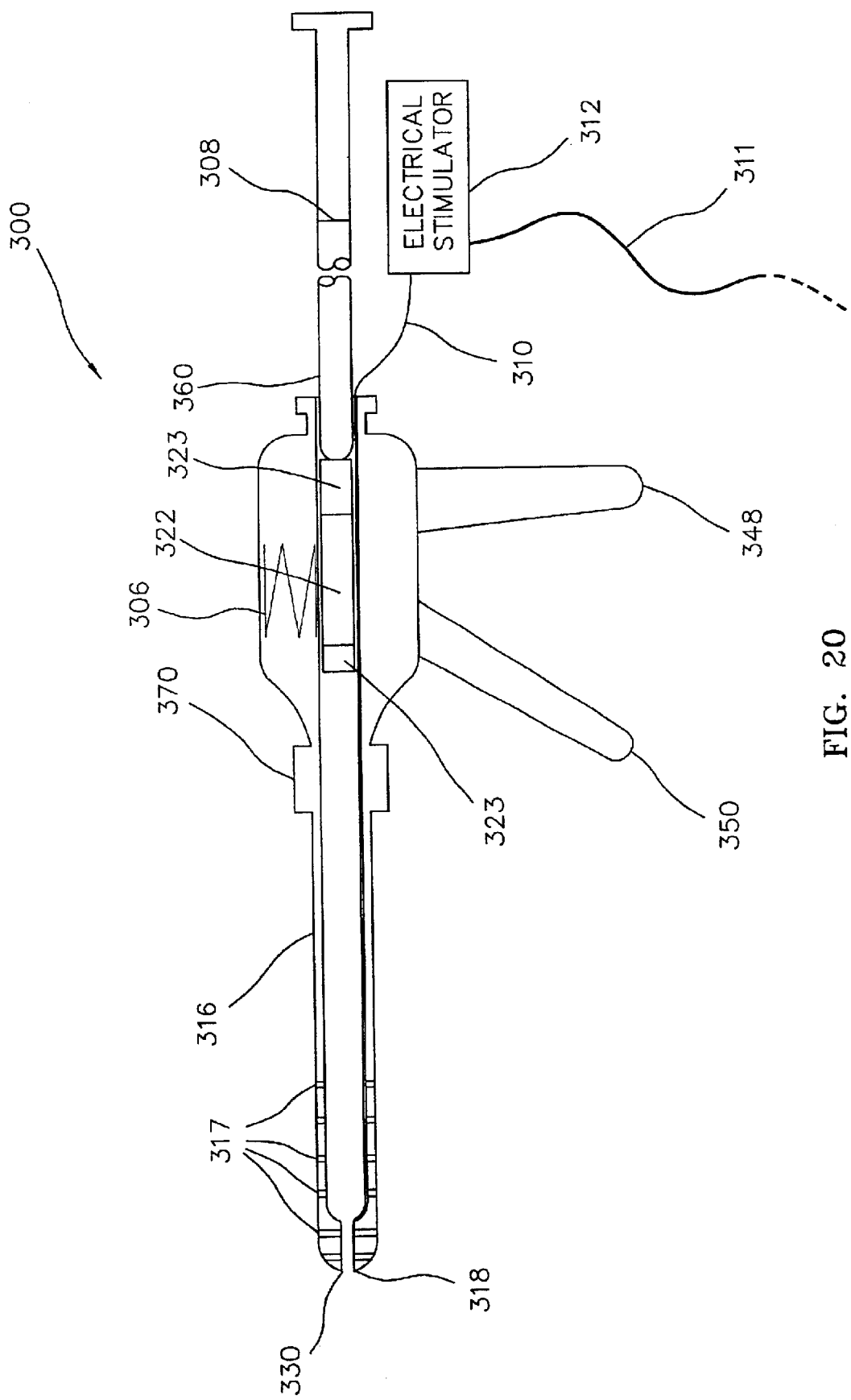
FIG. 20 illustrates a cross-sectional view of the implantation tool.

The electrode probe 302 is removed from the implantation tool 300 and the position of implantation tool 300 relative to the nerve (not illustrated) is determined by observing the muscle response when the nerve is stimulated by pulsing the electrical stimulator 312 (see FIG. 20). The electrical signal passes along sheath electrode wire 310, which passes down the length of implantation tool 300 along outer sheath 316 and to sheath electrode 318, which is located at the end of the implantation tool 300, next to the nerve being stimulated. The electrical stimulator 312 is preferably controlled by a foot control. A return electrode probe wire 311, attached from the skin to the electrical stimulator 312 near the implantation site, completes the electrical circuit.

Saline is preferably injected into the implantation tool 300. The saline facilitates obtaining a good electrical connection between the nerve, living tissue, and the microstimulator 322 which is about to be implanted. In a preferred embodiment (see FIG. 20), the microstimulator 322 has microstimulator electrodes 323 located on each end.

The plunger 360 is withdrawn from the implantation tool 300 (see FIG. 20) by moving ratcheting lever 350 with respect to handle 348, until the microstimulator 322 is moved into ejection position by ejection spring 306. The plunger 360 is then moved into the implantation tool 300 by reversing the direction set switch (not illustrated) and then moving ratcheting lever 350 with respect to handle 348. When plunger 360 is moved to a predetermined position, as indicated by a mark 308 on the plunger 360, then the microstimulator 322 is next to the aperture 330, as illustrated in FIG. 21.

In a preferred embodiment, the outer sheath 316 and the plunger 360 are made of an electrically non-conductive material, such as plastic. The outer sheath 316 and plunger 360 must be insulated or must be nonconductors to ensure that the electrical pulsing signals that are used to locate the nerve are not electrically shorted.

The holes 317, that are preferably located near the tip of the implantation tool 300 nearest the nerve, pass through the wall of the outer sheath 316. The holes 317 are located to correspond with the microstimulator 322 when it is ready to be ejected from the implantation tool 300, as illustrated in FIG. 21, to enable electrical contact between the microstimulator 322 and the living tissue.

Figure 21:
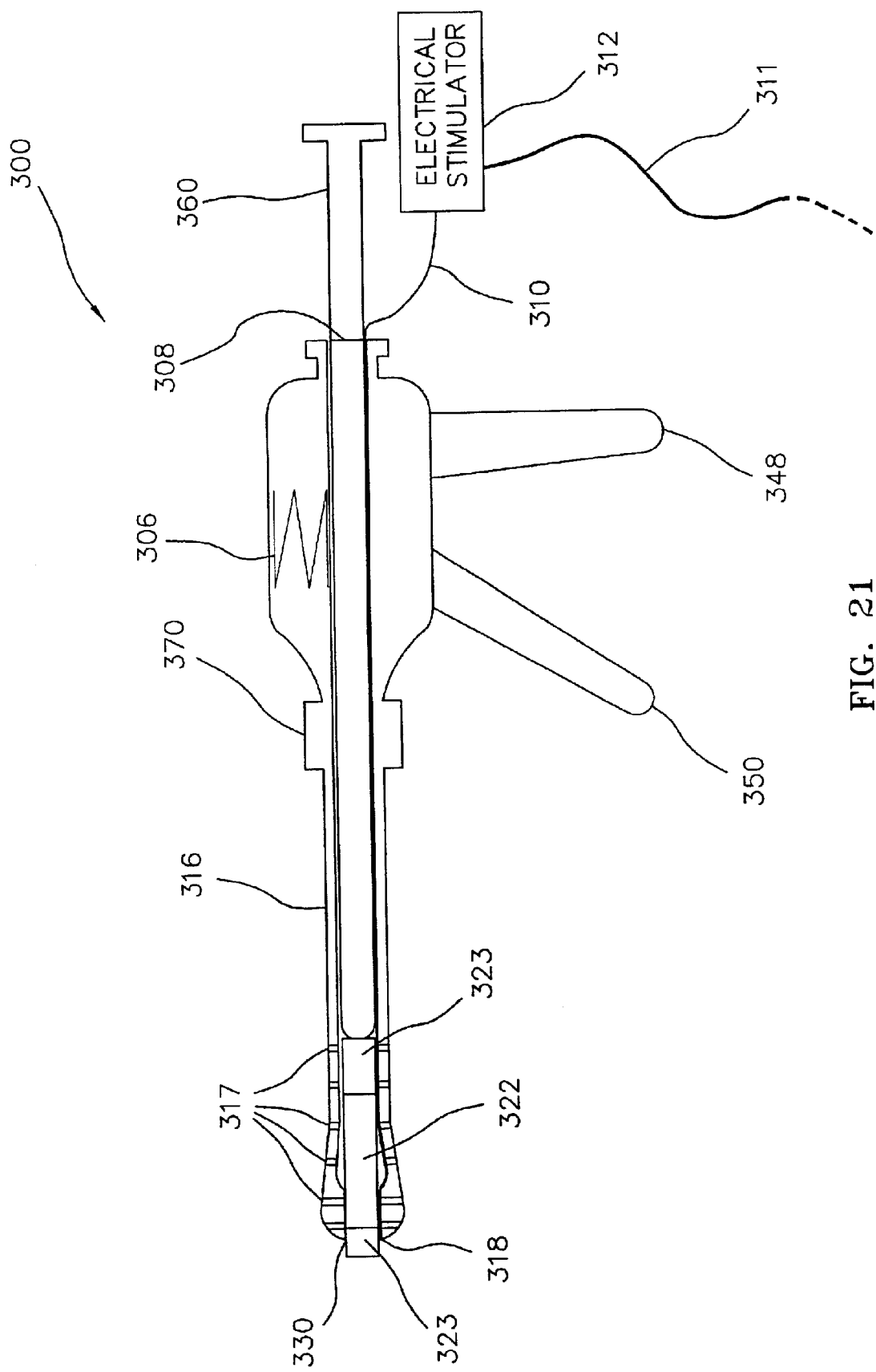
FIG. 21 illustrates a cross-sectional view of the implantation tool ejecting a microstimulator.

The electrical functions of the microstimulator 322 are preferably verified while it is retained in the outer sheath 316, near the nerve (see FIG. 21). The microstimulator 322 is ejected by continuing to move ratcheting lever 350 to force the microstimulator 322 through the aperture 330 by means of the plunger 360. During the ejection process, the implantation tool is slowly withdrawn from the living tissue and the microstimulator 322 is ejected to remain at the same relative position to the nerve.

The outer sheath 316 is removable from the implantation tool 300 by disassembling disconnect 370. This allows the outer sheath 316 portion of the implantation tool 300 to be removed and discarded or cleaned separately from the rest of the tool 300.

H. Ring Electrode for Placement of a Microstimulator

Figure 22:
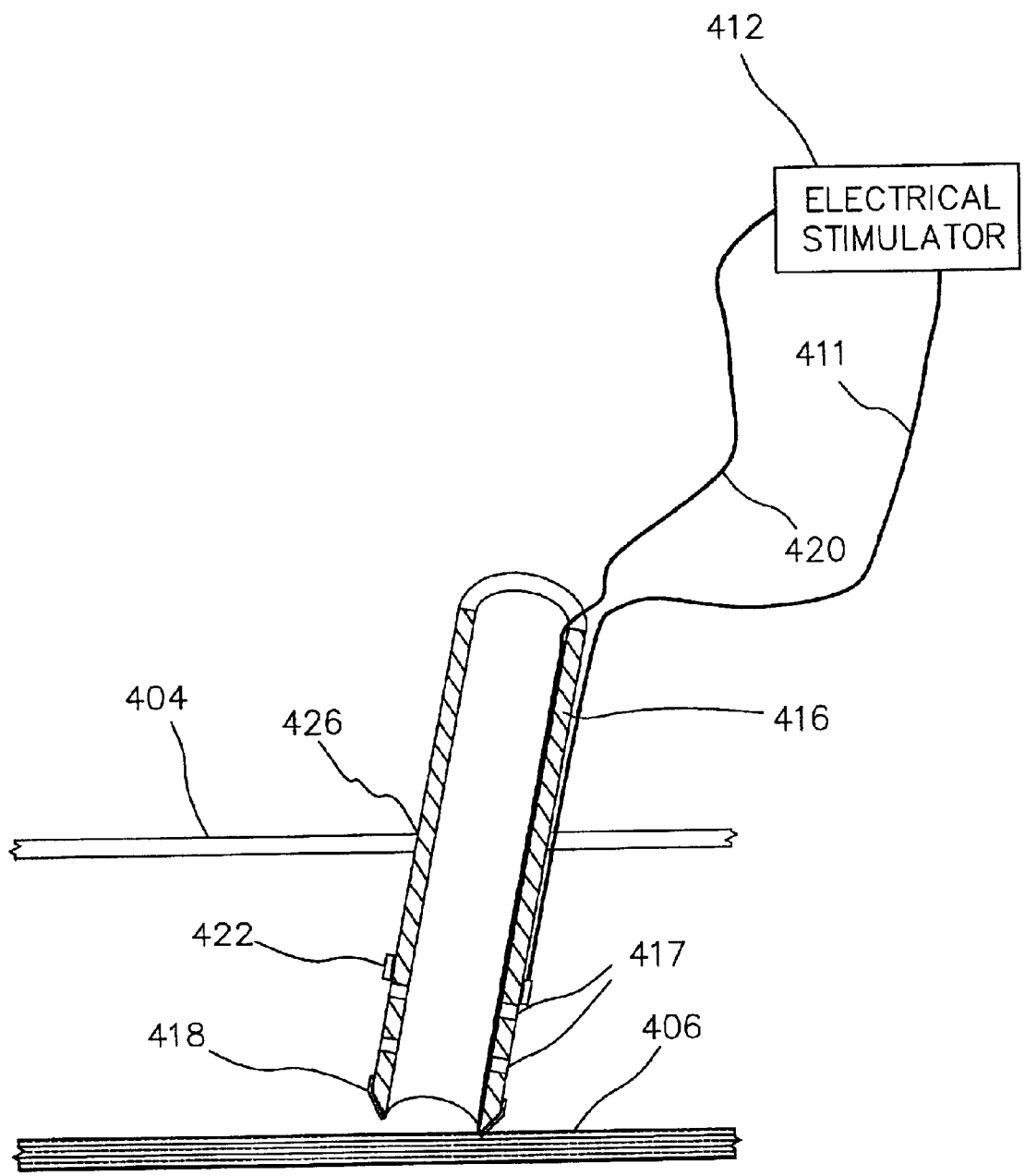
FIG. 22 depicts a cross-sectional view of the outer sheath and ring electrode near a nerve.

FIG. 22 depicts an alternative embodiment of the invention wherein there is a ring electrode 418 that is attached circumferentially at the sharpened tip of outer sheath 416 that is nearest the nerve 406. The outer sheath 416 passes through the skin 404 at the insertion point 426. The outer sheath 416 contains holes 417 which are located in the wall of the outer sheath 416 to facilitate electrical contact between the microstimulator (not shown) and the living tissue during insertion of the microstimulator in the tissue, but before the microstimulator has been ejected from the outer sheath 416. An electrical signal is generated by the electrical stimulator 412 that passes along sheath lead wire 420 to ring electrode 418. Ring electrode 418 is a conductive material that may be plated, deposited, mechanically bonded, or attached by any of the known processes for making a conductor that is integrally bonded to or a part of the sharpened tip of outer sheath 416. The sharpened tip end (i.e., inserted end) is referred to as the distal end of the outer sheath 416, while the opposite end of the outer sheath 416 is referred to as the proximal end. An advantage of having a ring electrode 418 over a single point electrode is that the possibility of damaging the nerve 406 with an electric pulse is reduced when the size of the electrode is increased.

I. Ring Return Electrode for Placement of a Microstimulator

FIG. 22 additionally depicts an alternative embodiment for a ring return electrode, wherein the ring return electrode 422 is located circumferentially around the outside of sheath 416. The ring return electrode 422 preferably acts as the cathode return element and completes the electrical circuit via the return electrode probe wire 411, which in turn connects to the electrical stimulator 412. The ring return electrode 422 is preferably located between the sharpened tip or distal end (i.e., the inserted end) and the proximal end of the sheath 416.

A benefit of utilizing the ring electrode 418 in conjunction with the ring return electrode 422 is that by locating ring return electrode 422 a distance from ring electrode 418 that approximates the distance between the electrodes on the microstimulator (not illustrated), the electrical resistivity that the microstimulator will encounter after being implanted in the living tissue can be measured before the microstimulator is ejected from the outer sheath 416. This allows a prediction of the battery life of the implanted microstimulator and gives the surgeon an opportunity to modify the implantation location, if the predicted life or performance of the microstimulator is not adequate.

The following nonlimiting example sets forth an exemplary procedure for implantation of a miniature implantable stimulator or sensor, e.g., the BION® that is available from Advanced Bionics Corporation, by using an embodiment of the present invention.

EXAMPLE

Microstimulator Implantation Procedure, Anterior Approach, for Sleep Apnea

1. Instruct the patient to lie down in the supine position.
2. Prepare the patient for surgery using standard surgical preparation.
3. Anesthetize the skin and subcutaneous tissue with 1% xylocaine/1:100,000 epinephrine at and around the insertion site in the neck.
4. Anesthetize one nostril and the nasopharynx with topical lidocaine/oxymetazoline solution and insert a laryngoscope to observe tongue movement during hypoglossal nerve stimulation.
5. Mark the midpoint of the hyoid bone and mark a point about 1 cm anterior/superior to the hyoid with a sterile pen. Make an incision about 1 cm wide parallel to the hyoid extending down into the subcutaneous tissue about 5 mm mid center over the 1 cm anterior point. Use an intravenous sedative as required.
6. Attach the electrical stimulator cathodal connecting lead to the proximal end of the blunt tipped electrode probe. The electrical stimulator anode lead is attached to a surface electrode placed on the exposed shoulder.
7. Insert the probe into the incision about 5–6 mm off the midline at a right angle to the skin. Advance the probe slowly inward at about 15 degrees laterally off the perpendicular toward the hypoglossal nerve.
8. Turn the electrical stimulator on (at approximately 30 pulses/sec, 3 mA, 200 $\mu$sec) and advance the probe slowly inward toward the hypoglossal nerve (HGN) until a contraction of the tongue is observed. Increase the stimulation current to 5–10 mA for brief periods, if required, to optimally position the probe. Check with the patient to ensure comfort at this level.
9. Remove the cathodal connecting lead from the probe. Connect the sheath lead wire to the electrical stimulator. Slide the inner sheath and outer sheath near the tip of the probe by observing location marks on the probe.
10. Turn the electrical stimulator on (at approximately 30 pulses/sec, 3 mA, 200 $\mu$sec) and advance the inner sheath and the outer sheath slowly toward the optimum position near the hypoglossal nerve (HGN) until a contraction of the tongue is observed. It may be necessary to increase the stimulation current to 5–10 mA for brief periods while searching for the optimum location for the best response of the muscle. Check with the patient to ensure comfort at this level.

11. While holding the inner sheath and outer sheath, pull the probe gently out of the inner sheath. Detach the outer sheath from the inner sheath. Holding the outer sheath, withdraw the inner sheath 3–4 cm.

12. Attach a 5 ml syringe, filled with normal sterile saline (0.9% NaCl), to the inner sheath and inject a few drops into the inner sheath, then remove the inner sheath. Then, insert the microstimulator into the outer sheath. The microstimulator is positioned by pushing it with the inner sheath, which is marked on its shaft to indicate when the tip microstimulator is at the tip of the outer sheath. Add more saline into the outer sheath through the inner sheath, ensuring that the anode will make electrical connection to the tissue through the small holes in the outer sheath's wall.

13. To ensure proper microstimulator position, turn the electrical stimulator on and confirm that a contraction of the tongue is observed when it is stimulated with the sheath electrode. Then activate the microstimulator external coil and controller. If the microstimulator does not contract the genioglossus muscle (GGM) adequately, then withdraw the microstimulator while it is still in the outer sheath. Then reposition the microstimulator using the outer sheath and sheath electrode to determine the optimum position. If the response is similar to that evoked using the electrical stimulator and probe, then pull the outer sheath gently up to the second mark on the inner sheath, while holding the inner sheath and microstimulator stationary in the fixed position, so the microstimulator is extruded and placed in position. After the microstimulator is extruded, remove the outer sheath and inner sheath from the patient, and then test the microstimulator again for position near the nerve using the external coil and controller. If the microstimulator has moved after being extruded from the outer sheath (verified by stimulation and poor GGM response while the microstimulator pickup electrodes indicate good coupling), then withdraw the microstimulator by the attached removal loop, and reintroduce using steps 10–13.

14. If the microstimulator is in the correct location and is able to stimulate the GGM satisfactorily, then the emerging removal loop is threaded onto a small curved needle and sewn to the subcutaneous tissues. Close the subcutaneous layer with dissolvable sutures and the skin with monofilament nylon sutures. Keep the skin sutures in place for approximately 10 days.

Obviously, many modifications and variations of the present invention are possible in light of the above teachings. For example, while the examples have generally referenced implantation of devices for nerve stimulation to invoke muscle stimulation, it is recognized that the muscle may be stimulated directly. Thus, any stimulation or sensing of any neuro-muscular pathway, i.e., nerve or muscle, with a microdevice, i.e., a microstimulator or microsensor, is applicable to the present invention. It is therefore to be understood that, within the scope of the appended claims, the invention may be practiced otherwise than as specifically described.

What is claimed is:

1. An insertion device for placement of a medical device proximate to a desired neuro-muscular pathway in living tissue, said insertion device comprising:

an outer sheath configured for receiving the medical device, said outer sheath having an electrical conductor configured for contacting the living tissue and passing an electric current to the living tissue for stimulating a neuro-muscular pathway for determining the proximity of the outer sheath to the neuro-muscular pathway in order to position said outer sheath near a neuro-muscular pathway so as to facilitate implantation of said medical device proximate to the neuro-muscular pathway.

2. The insertion device according to claim 1 further comprising an electrical stimulator electrically coupled to said electrical conductor.

3. An insertion device for placement of a medical device proximate to a desired neuro-muscular pathway in living tissue, said insertion device comprising:

an outer sheath configured for receiving said medical device, said outer sheath having an electrical conductor configured for contacting the living tissue and passing an electric current between said medical device and the living tissue for stimulating a neuro-muscular pathway for determining the proximity of the outer sheath to the neuro-muscular pathway in order to position said outer sheath near a neuro-muscular pathway so as to facilitate implantation of said medical device proximate to the neuro-muscular pathway; and wherein said outer sheath has a distal end, said distal end being sharpened.

4. An insertion device for placement of a medical device proximate to a desired neuro-muscular pathway in living tissue, said insertion device comprising:

an outer sheath configured for receiving said medical device, said outer sheath having an electrical conductor configured for contacting the living tissue and passing an electric current between said medical device and the living tissue for stimulating a neuro-muscular pathway for determining the proximity of the outer sheath to the neuro-muscular pathway in order to position said outer sheath near a neuro-muscular pathway so as to facilitate implantation of said medical device proximate to the neuro-muscular pathway; and wherein said outer sheath has a proximal end and a distal end and said outer sheath includes a ring electrode at said distal end that is coupled to said electrical conductor for contacting the living tissue.

5. An insertion device for placement of a medical device proximate to a desired neuro-muscular pathway in living tissue, said insertion device comprising:

an outer sheath configured for receiving said medical device, said outer sheath having an electrical conductor configured for contacting the living tissue and passing an electric current between said medical device and the living tissue for stimulating a neuro-muscular pathway for determining the proximity of the outer sheath to the neuro-muscular pathway in order to position said outer sheath near a neuro-muscular pathway so as to facilitate implantation of said medical device proximate to the neuro-muscular pathway;

wherein said outer sheath has a proximal end and a distal end and said outer sheath includes a ring electrode at said distal end that is coupled to said electrical conductor for contacting the living tissue; and a ring return electrode, located on said outer sheath between said proximal end and said distal end, to form an electrical return path.

6. An insertion device for placement of a medical device proximate to a desired neuro-muscular pathway in living tissue, said insertion device comprising:

an outer sheath configured for receiving said medical device, said outer sheath having an electrical conductor configured for contacting the living tissue and passing an electric current between said medical device and the living tissue for stimulating a neuro-muscular pathway for determining the proximity of the outer sheath to the neuro-muscular pathway in order to position said outer sheath near a neuro-muscular pathway so as to facilitate implantation of said medical device proximate to the neuro-muscular pathway; and wherein said outer sheath has a proximal end and a distal end and said electrical conductor comprises an electrically insulated wire located between said proximal end and said distal end.

7. An insertion device for placement of a medical device proximate to a desired neuro-muscular pathway in living tissue, said insertion device comprising:

an outer sheath configured for receiving said medical device, said outer sheath having an electrical conductor configured for contacting the living tissue and passing an electric current between said medical device and the living tissue for stimulating a neuro-muscular pathway for determining the proximity of the outer sheath to the neuro-muscular pathway in order to position said outer sheath near a neuro-muscular pathway so as to facilitate implantation of said medical device proximate to the neuro-muscular pathway; and wherein said outer sheath is substantially cylindrically shaped having an outer diameter and an inner diameter defining a wall therebetween and wherein said electrical conductor comprises an insulated wire located inside said wall of said outer sheath.

8. The insertion device according to claim 1 wherein said outer sheath is substantially cylindrically shaped having an outer diameter and an inner diameter defining a wall therebetween and wherein said electrical conductor comprises an electrical conductor located inside said wall of said outer sheath.

9. An insertion device suitable for placement of a medical device proximate to a desired neuro-muscular pathway in living tissue, said insertion device comprising:

an inner sheath capable of forcing said medical device through an outer sheath, said outer sheath surrounding said inner sheath, said outer sheath having an electrical conductor configured for contacting the living tissue and passing an electric current to the living tissue for stimulating a neuro-muscular pathway for positioning said outer sheath near a neuro-muscular pathway so as to facilitate implantation of said medical device proximate to the neuro-muscular pathway.

10. The insertion device according to claim 9 further comprising an electrical stimulator electrically coupled to said electrical conductor.

11. The insertion device according to claim 9 wherein said inner sheath has a distal end, said distal end being sharpened.

12. An insertion device suitable for placement of a medical device proximate to a desired neuro-muscular pathway in living tissue, said insertion device comprising:

an inner sheath capable of forcing said medical device through an outer sheath, said outer sheath surrounding said inner sheath, said outer sheath having an electrical conductor configured for contacting the living tissue and passing an electric current between said medical device and the living tissue for stimulating a neuro-muscular pathway for positioning said outer sheath near a neuro-muscular pathway so as to facilitate implantation of said medical device proximate to the neuro-muscular pathway; and wherein said outer sheath has a distal end, said distal end being sharpened.

13. An insertion device suitable for placement of a medical device proximate to a desired neuro-muscular pathway in living tissue, said insertion device comprising:

an inner sheath capable of forcing said medical device through an outer sheath, said outer sheath surrounding said inner sheath, said outer sheath having an electrical conductor configured for contacting the living tissue and passing an electric current between said medical device and the living tissue for stimulating a neuro-muscular pathway for positioning said outer sheath near a neuro-muscular pathway so as to facilitate implantation of said medical device proximate to the neuro-muscular pathway; and wherein said outer sheath has a distal end and said outer sheath includes a ring electrode at said distal end that is coupled to said electrical conductor for contacting the living tissue.

14. An insertion device suitable for placement of a medical device proximate to a desired neuro-muscular pathway in living tissue, said insertion device comprising:

an inner sheath capable of forcing said medical device through an outer sheath, said outer sheath surrounding said inner sheath, said outer sheath having an electrical conductor configured for contacting the living tissue and passing an electric current between said medical device and the living tissue for stimulating a neuro-muscular pathway for positioning said outer sheath near a neuro-muscular pathway so as to facilitate implantation of said medical device proximate to the neuro-muscular pathway;

wherein said outer sheath has a distal end and said outer sheath includes a ring electrode at said distal end that is coupled to said electrical conductor for contacting the living tissue; and wherein said outer sheath has a proximal end, said outer sheath additionally comprising a ring return electrode located on said outer sheath between said proximal end and said distal end to form an electrical return path.

15. A method of placing an implantable medical device proximate to a desired neuro-muscular pathway in living tissue, said method comprising the steps of:

inserting an inner sheath and an outer sheath into a desired location of a patient's body, said inner sheath being removably housed within said outer sheath;

stimulating the neuro-muscular pathway by conducting electricity through said outer sheath for determining the position of said outer sheath relative to the neuro-muscular pathway;

removing said inner sheath;

inserting said implantable medical device through said outer sheath until said implantable medical device is positioned proximate to the neuro-muscular pathway; and removing said outer sheath.

16. An insertion device for placement of a implantable microdevice proximate to a neuro-muscular pathway in living tissue, said implantable microdevice adapted for neuro-muscular stimulation and sensing proximate to a desired neuro-muscular pathway in living tissue said system comprising:

an outer sheath and an inner sheath adapted for penetration into living tissue said inner sheath being a hollow tube having an outside diameter that is approximately equal to an outside diameter of said implantable microdevice and removably insertable into said outer sheath, such that when said inner sheath is inserted into said outer sheath, said inner sheath may be suitable to be removably insertable into the living tissue; and wherein said outer sheath comprises an electrical conductor for conducting electric current; and wherein said outer sheath comprises an outer sheath electrode coupled to said electrical conductor and adapted for contacting living tissue for stimulating the neuro-muscular pathway for determining the proximity of said outer sheath to the neuro-muscular pathway, so as to facilitate implantation of said microdevice proximate to the neuro-muscular pathway.

17. The insertion device according to claim 16 further comprising:
   a rigid electrode probe, having a sharpened end, said probe being removably insertable into said inner sheath; and
   said electrode probe being electrically conductive at said sharpened end and adapted for contacting and electrically stimulating desired living tissue.

18. The insertion device according to claim 17 wherein said electrode probe is electrically coupled to and energized by a foot-operated switch.

19. The insertion device according to claim 16 wherein said outer sheath is substantially cylindrically shaped having an outer diameter and an inner diameter defining an inner surface and an outer surface and wherein said electrical conductor is an insulated wire that is located along said inner surface of said outer sheath.

20. The insertion device according to claim 16 wherein said outer sheath is substantially cylindrically shaped having an outer diameter defining an outer surface and an inner diameter defining an inner surface and wherein said electrical conductor is an insulated wire that is located along said outside surface of said outer sheath.

21. The insertion device according to claim 16 wherein said outer sheath is substantially cylindrically shaped having an outer diameter defining an outer surface and an inner diameter defining an inner surface and wherein said electrical conductor is an insulated wire that is located inside said wall of said outer sheath.

22. The insertion device according to claim 16 wherein said electrical conductor is a ring electrode.

23. The insertion device according to claim 16 wherein an outer sheath is substantially cylindrically shaped having an outer diameter defining an outer surface and an inner diameter defining an inner surface and wherein a ring return electrode is located on said outer surface of said outer sheath to form an electrical return path.

24. The insertion device according to claim 16 wherein said outer sheath is substantially cylindrically shaped having an outer diameter and an inner diameter defining a wall therebetween and wherein said electrical conductor is a conductive path of metal that is located in said wall of said outer sheath.

25. The insertion device according to claim 16 additionally comprising a blunt-end push rod, which is removably insertable into said outer sheath and is configured for pushing said microdevice through said outer sheath and into proximity to the neuro-muscular pathway.

26. The insertion device according to claim 16 wherein said implantable microdevice comprises:

a hermetically-sealed housing;
at least two exposed electrodes for passing an electrical signal between said microdevice and the surrounding tissue; and
electronic circuit means within said housing for generating or receiving an electrical signal.

27. A method of placing a microdevice proximate to a neuro-muscular pathway in living tissue when it is located near the neuro-muscular pathway, said method comprising the steps of:
   inserting an electrode probe in the living tissue to locate near the neuro-muscular pathway;
   electrically stimulating the neuro-muscular pathway with said electrode probe;
   monitoring a neuro-muscular response to verify the location of said electrode probe with respect to the neuro-muscular pathway;
   placing an outer sheath and an inner sheath around said electrode probe;
   positioning said outer sheath and said inner sheath near the neuro-muscular pathway;
   removing said electrode probe;
   electrically stimulating the neuro-muscular pathway with said outer sheath to verify the location of said outer sheath with respect to the neuro-muscular pathway;
   inserting said microdevice through said outer sheath into the living tissue; and
   confirming the location of said microdevice with said outer sheath by electrically stimulating the neuro-muscular pathway and detecting a response thereto before removing said outer sheath.

28. The method of claim 27 further comprising confirming the location of said microdevice near the neuro-muscular pathway, prior to ejecting said microdevice from said outer sheath, by electrically stimulating the neuro-muscular pathway by passing an electric current from an electrical stimulator along an outer sheath lead wire to an outer sheath electrode located on said outer sheath and detecting a response thereto.

29. The method of claim 27 further comprising removing said microdevice from the living tissue with said outer sheath if said microdevice has not been ejected from said outer sheath.

30. An insertion device for placement of a microdevice for modifying or affecting a body parameter when said microdevice is located near a desired neuro-muscular pathway in living tissue, said microdevice substantially cylindrically shaped having an outer diameter, said system comprising:
   an outer sheath having a distal end, said distal end being sharp and being expandable to allow said microdevice to be ejected therethrough, wherein said outer sheath is a substantially cylindrically shaped hollow tube having an inner diameter approximately equal to said outer diameter of said microdevice, said outer sheath being sized to temporarily house said microdevice, wherein said outer sheath is removably insertable into the living tissue;
   an electrical conductor forming a part of said outer sheath; and wherein
   said outer sheath contains an electrode located on said distal end configured for contacting the living tissue and that is electrically connected to said electrical conductor for passing an electrical signal between said insertion device and the living tissue to confirm that said distal end is suitably positioned near the neuro-muscular pathway.

31. The insertion device according to claim 30 wherein said outer sheath has an outer diameter defining an outer surface, said electrode comprising a ring electrode on said outer surface that is coupled to said electrical signal conducting means.

32. The insertion device according to claim 31 wherein a ring return electrode is located on said outer surface of said outer sheath to form an electrical return path.

33. An implantation device for placement of a microdevice for modifying or affecting a body parameter when said microdevice is located near a desired neuro-muscular pathway in living tissue, said microdevice being substantially cylindrically shaped having an outer diameter, said device comprising:

an outer sheath being substantially cylindrically shaped having an inner diameter that defines a hollow center with said internal diameter slightly larger than said outer diameter of said microdevice that is to pass through said hollow center, wherein said outer sheath has a distal end that is sharpened for penetrating living tissue and further has an aperture that passes through said distal end;

an outer sheath connection means for attaching to said implantation device;

a plunger that is removably insertable into said hollow center of said outer sheath;

a ratcheting lever actuateable for causing said plunger to slide in said hollow center toward said distal end; and means for conducting an electrical signal along said outer sheath to a sheath electrode that is located at said distal end.

34. The implantation device according to claim 33 wherein said sheath electrode comprises a ring electrode coupled to means for conducting an electrical signal.

35. The implantation device according to claim 33 wherein a ring return electrode is located on said outer sheath to form an electrical return path.

36. The implantation device according to claim 33 additionally comprising means for placing sold microdevice into said hollow center of said outer sheath to enable placement of said microdevice at said distal end of said outer sheath.

37. The implantation device according to claim 33 further comprising:

an elongated electrode probe having an outer diameter, said plunger being substantially cylindrical in cross-section, said plunger having a length and an inner diameter defining a passageway extending longitudinally along said length thereof, said inner diameter of said probe being slightly larger than said outer diameter of said electrode probe; and wherein said electrode probe is removably insertable into said plunger.

38. An insertion device for placement of an implantable medical device proximate to a neuro-muscular pathway in living tissue, said insertion device comprising:

an outer sheath, having an expandable sharpened tip for penetrating the living tissue, said tip being expandable to allow said implantable medical device to be removably ejected from said outer sheath; and an electrical conductor forming a part of said outer sheath, wherein said electrical conductor is configured for contacting the living tissue and passing an electric current to the living tissue in order to facilitate positioning said outer sheath near the neuro-muscular pathway.

39. An insertion device adaptable for placement of an implantable medical device proximate to a neuro-muscular pathway in living tissue, wherein said implantable medical device having an axial dimension of less than 60 mm and a lateral dimension of less than 6 mm, said system comprising an outer sheath configured for at least partially containing said implantable medical device, wherein said outer sheath has an outer diameter and an inner diameter defining a wall, said wall defining at least one through hole in said wall, said hole located to enable electrical contact between said implantable medical device while contained in said outer sheath and the living tissue.

40. The insertion device according to claim 39 wherein said medical device is a microstimulator.

41. The insertion device according to claim 39 wherein said medical device is a microsensor.

* * * * *